US009066483B2

(12) United States Patent
Chungu et al.

(10) Patent No.: US 9,066,483 B2
(45) Date of Patent: Jun. 30, 2015

(54) LOW FIBER YELLOW CANOLA SEEDS COMPRISING HIGH, OLEIC, LOW LINOLENIC OIL

(75) Inventors: Chibwe Chungu, Visalia, CA (US); Gerhard Rakow, Saskatoon (CA); John P. Raney, Saskatoon (CA); Thomas J. Kubik, Saskatoon (CA); Barbara L. Raney, legal representative, Clavet (CA)

(73) Assignees: Her Majesty the Queen in Right of Canada as represented by the Minister of Agriculture and Agri-Food, Saskatoon, Saskatchewan (CA); Dow AgroSciences LLC, Indianapolis ( * ) Notice: Subject to any disclaimer, the term of this patent is extended or adjusted under 35 U.S.C. 154(b) by 1808 days.

(21) Appl. No.: 11/997,225

(22) PCT Filed: Aug. 1, 2006

(86) PCT No.: PCT/US2006/029813
§ 371 (c)(1),
(2), (4) Date: May 25, 2010

(87) PCT Pub. No.: WO2007/016521
PCT Pub. Date: Feb. 8, 2007

(65) Prior Publication Data
US 2010/0303999 A1     Dec. 2, 2010

Related U.S. Application Data

(60) Provisional application No. 60/704,469, filed on Aug. 1, 2005.

(51) Int. Cl.
*A01H 5/10*     (2006.01)
(52) U.S. Cl.
CPC ......................................... *A01H 5/10* (2013.01)
(58) Field of Classification Search
None
See application file for complete search history.

(56) References Cited

U.S. PATENT DOCUMENTS

| 6,063,947 | A | 5/2000 | Debonte et al. | |
|---|---|---|---|---|
| 6,433,254 | B1 * | 8/2002 | Sernyk | 800/306 |
| 6,455,763 | B1 * | 9/2002 | Sernyk | 800/306 |
| 6,489,543 | B1 | 12/2002 | Sernyk | |
| 6,720,481 | B1 | 4/2004 | Patel et al. | |
| 2002/0124283 | A1 | 9/2002 | Facciotti | |
| 2003/0159176 | A1 | 8/2003 | Debonte et al. | |

FOREIGN PATENT DOCUMENTS

| WO | WO 98/49889 | 11/1998 |
|---|---|---|
| WO | WO 02/063018 A2 | 8/2002 |
| WO | WO 2004/072259 | 8/2004 |

OTHER PUBLICATIONS

Scarth, R., et al., Designer Oil Canola—a Review of new Food-Grade Brassica Oils with Focus on High Oleic, Low Linolenic Types, Proceedings of the 10th International Rapeseed Congress, Canberra, Australia, 1999, XP002513934.
Friedt, W., et al., Breeding of Rapeseed (*Brassica napus*) for Modified Seed Quality—Synergy of Conventional and Modern Approaches, Proceedings of the 10th International Rapeseed Congress, Canberra, Australia, 1999, XP002513935.
Rakow, G., et al., BO 5.1: Present Status and Future Perspectives of Breeding for Seed Quality in Brassica Oilseed Crops, Proceedings of the 11th International Rapeseed Congress, Copenhagen, Denmark, Jul. 2003, vol. 1, p. 181-185, XP008101675.
Relf-Eckstein, J., et al. Yellow Seeded *Brassica napus* Canola—A New Generation of High Quality Canola for Canada; Proceedings of the 11th Int. Rapeseed Congress, Copenhagen, Denmark, Jul. 2003, vol. 2, p. 458-460, XP008101674.
O'Sullivan, Ashley, Canadian Canola—Setting a New World Standard for Quality, WWW.Seedquest.com [online], Mar. 2004, p. 1, XP002513936, Retrieved from the Internet: URL:http://www.seedquest.com/News/releases/2004/march/7913.htm.
Jiang, P., Chemical Composition and Nurtitive Value of Yellow-Seeded *Brassica napus* Canola and Canola-Quality Sinapis Alba Mustard for Poultry:, Thesis, The University of Manitoba, Apr. 1999, XP002513937.
Burbulis, N., A New Yellow-Seeded Canola Genotype Originating from Double Low Black-Seeded *Brassica napus* Cultivars, Canadian Journal of Plant Science, vol. 85, No. 1, Jan. 2005, pp. 109-114, XP002513938; ISSN: 0008-4220.
Slominski, B., Nutritive Value for broilers of meals Derived from Newly Developed Varieties of Yellow-Seeded Canola, Animal Feed Science and technology, vol. 78, No. 3-4, Apr. 1999, p. 249-262, XP002513939; ISSN: 0377-8401.
Simbaya, J., et al., Quality Characteristics of Yellow-Seeded Brassica Seed Meals: Protein, Carbohydrates, and Dietary Fiber Components, Journal of Agricultural and Food Chemistry, vol. 43, No. 8, 1995, p. 2062-2066, XP002513940, ISSN: 0021-8561.
Daun, J., et al., Quality of Yellow and Dark Seeds in Brassica-Campestris Conola Varieties Candle and Tobin, Jaocs (Journal of the American Oil Chemists' Society), vol. 65, No. 1, 1998, p. 122-126, XP008101617, ISSN: 0003-021X.

* cited by examiner

*Primary Examiner* — Elizabeth McElwain
(74) *Attorney, Agent, or Firm* — Faegre Baker Daniels LLP

(57) ABSTRACT

The subject invention provides low fiber, yellow-seeded canola, and related canola meal and animal feed. Oil produced from this seed has at least 68% oleic acid and no more than 3% linolenic acid, relative to the total fatty acids in the oil. Specific canola lines exhibiting these characteristics are also provided. Canola seed offering the combined advantages of excellent oil together with high-quality meal has not heretofore been provided.

19 Claims, No Drawings

LOW FIBER YELLOW CANOLA SEEDS COMPRISING HIGH, OLEIC, LOW LINOLENIC OIL

CROSS-REFERENCE TO RELATED APPLICATION

The subject application is the U.S. national stage application of International Patent Application No. PCT/US2006/029813, filed Aug. 1, 2006, which claims priority to U.S. provisional application Ser. No. 60/704,469, filed Aug. 1, 2005.

BACKGROUND OF THE INVENTION

Canola is an important oil crop. Canola oil is considered to be a superior edible oil due to its low levels of saturated fatty acids. "Canola" refers to rapeseed (*Brassica* spp.) that has an erucic acid (C22:1) content of at most 2 percent by weight (compared to the total fatty acid content of a seed) and that produces (after crushing) an air-dried meal containing less than 30 micromoles (µmol) of glucosinolates per gram of defatted (oil-free) meal. These types of rapeseed are distinguished by their edibility in comparison to more traditional varieties of the species.

Regular canola oil (extracted from natural and earlier commercial varieties of rapeseed) is relatively high (8%-10%) in α-linolenic acid content ($C_{18:3}$) (ALA). This fatty acid is unstable and easily oxidized during cooking, which in turn creates off-flavors of the oil. It also develops off odors and rancid flavors during storage.

It is known that reducing the α-linolenic content level by hydrogenation increases the oxidative stability of the oil. Hydrogenation is routinely used to reduce the polyunsaturates content of vegetable oils. The food industry has used hydrogenation to raise the melting point of vegetable oils, leading to the creation of oil-based products with textures similar to butter, lard and tallow. During hydrogenation, trans isomers of unsaturated fatty acids are commonly produced. However, the nutritional properties of trans fatty acids mimic saturated fatty acids, thereby reducing the overall desirability of hydrogenated oils.

The development of NATREON (a trademark of Dow AgroSciences) oil has created an even healthier canola oil and increased the oxidative stability of the oil. NEXERA seeds are related. NATREON canola oil typically has over 70% oleic acid (C18:1) and less than 3% linolenic acid (C18:3). The dietary effects of high oleic and low linolenic have been shown to have dramatic effects on health by lowering the low-density lipoproteins (LDL) and have little or no adverse effects in the high-density lipoproteins. LDLs mediate the deposition of cholesterol on blood vessels leading to artherosclerosis and coronary heart disease. U.S. Pat. No. 6,489,543 (SV095-08); U.S. Pat. No. 6,433,254 (Nex 705); U.S. Pat. No. 6,455,763 (S010); and U.S. Pat. No. 6,444,879 (1709) relate to agronomically superior high oleic canola varieties. U.S. Pat. Nos. 5,965,755 and 6,169,190 (AG019) relate to high oleic, low linolenic acid canola oil.

Although rapeseed meal is relatively high in protein, its high fiber content decreases its digestibility and its value as an animal feed. Compared to soybean meal, regular canola meal contains higher values of dietary fiber. Because of its high dietary fiber, canola meal has about 20% less metabolizable energy (ME) than soybean meal. As a result, the value of the meal has remained low relative to other oilseed meals such as soybean meal. Rakow (2004a) reports that canola meal is sold for about 60-70% of the price of soybean meal mainly because of the high fiber content of canola meal (about 12% crude fiber) compared to soybean meal (about 4% crude fiber), which reduces its feed value particularly in rations for pigs and poultry. Canola meal contains approximately 36-38% crude protein whereas soybean meal contains 48% on an as-is basis. Also, the presence of glucosinolates decreases the value of some canola meal due to the deleterious effects these compounds have on the growth and reproduction of livestock.

In canola, most genetic selection to date has been focused on oil content and agronomic characteristics. The improvement of meal quality in *Brassica napus* canola must focus on increasing the metabolizable energy (ME) content of the meal in order to make it more competitive with other high protein feed such as soybean meal in rations for monogastric animals. Reduction in fiber levels would increase the nutritive value of canola meal by elevating the ratio of protein and ME.

Canola with yellow seed coats have been found to have thinner hulls and thus less fiber and more oil and protein than varieties with dark color seed coats. Seed coat color is generally divided into two main classes, yellow or black (or dark brown), although varying shades of these colors, such as reddish brown and yellowish brown, are also observed. Seed-coat color in rapeseed may be different depending on the particular species and variety of *Brassica*. Yellow-seeded rapeseed varieties are common in Asian countries, and in China, there is an abundance of yellow-seeded cultivars in production, particularly in *B. juncea* and *B. rapa* varieties.

Stringam et al. (1974) reported that yellow seeds of *B. rapa* had higher oil, higher protein, and lower fiber content than brown seeds. Bell & Shires (1982) studied the composition of yellow and brown canola seed hulls and compared their digestibility by pigs. The brown hulls contained more fiber and lignin. Shirzadegan & Robbelen (1985) reported an average of 2.6% higher oil and protein content in brown versus black seeds, and a 3% reduction in fiber and hull contents of yellow and brown seeds compared to common black seeded forms.

Bell (1995) noted that canola meal had high nutritional quality but the presence of hulls in the meal reduced the levels of available energy and protein, as well as amino acids and minerals. The nutritional value of canola meal can be improved by reducing fiber and/or hull contents, leading to greater digestibility of available protein and amino acids. The development of yellow-seeded varieties with less hull is offered as a possibility to increase the feed value of canola meal.

Simbaya et al. (1995) compared yellow-seeded meals from *B. napus, B. juncea*, and *B. rapa* to brown-seeded canola. On average, yellow-seeded samples had higher protein and lower dietary fiber (and lignin).

Getinet & Rakow (1997) studied the inheritance patterns of seed coat pigmentation repression in *B. carinata*. Slominski et al. (1999) compared the nutritive value for broiler chickens fed meals derived from these lines/varieties.

For more than 20 years, Agriculture and Agri-Food Canada (AAFC)-Saskatoon has conducted research towards the development of yellow-seeded *B. napus* and has produced different sources of yellow-seeded *B. napus* germplasm (Rashid et al. 1994; Rashid & Rakow 1995; Rakow et al. 1999 a & b; and Relf-Eckstein et al. 2003), the latter of which compares YN97-262 and three other yellow seeded lines to 46A65.

Rashid et al. (1994) relates to an interspecific crossing scheme used to develop yellow-seeded *B. napus* (with traits such as improved fertility). Rakow et al. (1999a) notes that in *B. napus*, no yellow-seeded types occur naturally; all have been developed through inter-specific hybridizations with *B. napus, B. juncea*, and *B. rapa* in various crossing combinations. Early lines had lower oil content than black seed lines (attributed to poor embryo development), were low yielding, and highly susceptible to blackleg (*Leptosphaeria maculans*). Rakow et al. (1999b) relates to a "much needed" new source of yellow-seeded *B. napus*, which was developed from interspecific crosses between black-seeded WESTAR and yellow-seeded *B. juncea* and *B. carinata*. The yellow-seeded lines thus obtained were reported to have low erucic acid, low glucosinolates, 60-65% oleic acid, 18-20% linoleic acid, and 7-9% linolenic acid.

Rakow (2004b) reports that yellow-seeded *Brassica* oil seeds have significantly reduced meal fiber levels and increased seed oil content, as compared to black or brown-seeded forms. This reference discusses results of a December 2003 report where yellow-seeded line YN01-429 was compared to black-seeded 46A65. The results are as follows:

TABLE 1

|  | YN01-429 | 46A65 |
|---|---|---|
| Yield (kg/ha) | 1640 | 1520 |
| Color (WIE*) | −46.6 | 1.9 |
| Seed Oil % | 47.86 | 43.88 |
| Meal Protein % | 52.55 | 54.27 |
| Seed Weight (g/1000s) | 3.33 | 2.79 |
| glucosinolates (umol/g) | 11.1 | 14.1 |
| TSAT % | 6.58 | 6.91 |
| C22:1 | 0.016 | 0.021 |
| Blackleg (% Westar) | 53 | 15 |
| ADF % meal | 9.62 | 15.69 |
| ADL % meal | 1.82 | 7.36 |

(*color was measured by method E313, white index)

This reference also reports of an increasing demand for high oleic/low linolenic acid, heat-stable, low trans fatty acid vegetable oils for frying applications. This reference reports of a desire to reduce fiber content and glucosinolate content to enhance the overall nutritional value of canola meal to meet an increasing demand for plant-based, high protein meal sources for the feed industry. This reference further reports that germplasm lines with low total saturated fat content (4.5-5.0%), low total glucosinolate content (<3 µmoles/gram of seed), high seed weight (>3 gram/100 seeds) and disease resistance have been developed in yellow-seeded forms of *B. napus*, and that future goals include continuing to increase such gene pools, and increasing meal protein content and seed size.

Rakow & Raney (2003) notes that rapeseed (canola) oil is high in oleic acid and essential polyunsaturated fatty acids, and that further oil quality improvements would include the development of very high oleic acid/low linolenic acid (HOLL) varieties for use in frying applications, and the creation of low and very low (zero) saturated fat oils. According to this reference, meal quality improvements will focus on fiber reductions (especially lignin) through the creation of yellow-seeded *B. napus* forms. Reduction or elimination of glucosinolates is listed as a further breeding goal. This reference further notes that new *Brassica* oil seed crops, such as *B. juncea* and *B. carinata*, are under development, but it is noted that each species has specific seed oil and meal quality challenges that need to be addressed, including modification of fatty acid compositions to improve oil quality.

Improved oil levels and protein levels are primary objectives of rapeseed breeding programs. Thus, introduction of a yellow seed coat trait into canola varieties is desirable, in the interest of providing improvements in both the seed oil and protein levels. However, integration of genes controlling seed pigmentation from related *Brassica* species into valuable oilseed *Brassica* varieties, such as canola varieties, is complicated by the fact that multiple recessive alleles are involved in the inheritance of yellow seed coats in presently available yellow seeded lines. Pod curling is also a common problem due to poor chromosome pairing when yellow-seed color is introgressed from other *Brassica* species, such as *juncea* and *carinata*.

U.S. Pat. Nos. 6,547,711 and 6,380,466 relate to rapeseed having a yellow-seed coat controlled by a single locus mutation. EP 1 031 577 relates to a *Brassica* plant transformed with a transparent seed coat gene.

The development, and potential advantages, of yellow-seeded canola combined with having certain advantageous oil profiles has not heretofore been achieved.

BRIEF SUMMARY OF THE INVENTION

The subject invention provides yellow-seeded canola that can be used to produce not only oil having advantageous fatty acid profiles (more than 68% oleic acid, by weight, and less than 3% linolenic acid, relative to total fatty acids) but also highly nutritious meal for animals such as chickens. Canola seed of the subject invention offers the highly advantageous combination of health oil (for the cooking industry and the like) together with high-protein, low-fiber animal feed. This combination has not heretofore been available from a single type of seed.

DETAILED DESCRIPTION OF THE INVENTION

Canola oil refers to oil extracted from commercial varieties of rapeseed. To produce canola oil, seed is typically graded and blended at grain elevators to produce an acceptably uniform product. The blended seed is then crushed, the oil is typically extracted with hexane, and then refined. The resulting oil is then sold for use. Oil content is typically measured as percent of the whole dried seed and is characteristic of different varieties of canola. (Oil content can be determined using various analytical techniques such as NMR, NIR, and Soxhlet extraction.) Percentage of total fatty acids is typically determined by extracting a sample of oil from seed, producing the methyl esters of fatty acids present in that oil sample, and analyzing the proportions of the various fatty acid in the sample using gas chromatography. The fatty acid composition can also be a distinguishing characteristic of a variety.

While canola oil, in general, has been recognized as very healthful oil, the meal component of the seed (left over after extracting the oil component) is inferior to (and not economically competitive with) soybean meal because of the high fiber content (and corresponding decreased nutritional value). Thus, the subject invention provides a highly nutritious and economical source of animal feed—canola meal—which has heretofore been a lower-value by product is now. The subject invention provides for recapturing value from this "byproduct." Thus, the subject invention also saves valuable resources.

The subject invention relates in part to yellow-seeded canola capable of yielding canola oil having a NATREON-type oil profile. As used herein, a "NATREON-type" or "NATREON-like" oil profile signifies an oleic acid content preferably in a range of 68-80%, 70-78%, 71-77%, and 72-75% (more preferably), all with an alpha linolenic content below 3%. The subject invention, however, is not limited to yellow seeds that yield such oils, but includes oil from such seeds having an oleic acid content greater than 80%, for example. There are many ways known in the art for measuring such fatty acid content. Preferred measurement methods are discussed herein, particularly in the Examples. Oils of the subject invention are naturally stable; they are not artificially hydrogenated.

Thus, the subject invention includes, in some embodiments, yellow canola seeds comprising an oil fraction and a meal fraction, said oil fraction having an α-linolenic acid content of 3% or less relative to the total fatty acid content of said seeds, and an oleic acid content of 68% or more relative to the total fatty acid content of said seeds. By definition, the erucic acid (C22:1) content is also less than 2 percent by weight (compared to the total fatty acid content of a seed), and each gram of defatted (oil-free) meal (after crushing and an air-drying) contains less than 30 micromoles (μmol) of glucosinolates.

The yellow color of the seeds is significant because it corresponds with improved nutritional characteristics of the meal component obtained after extraction of the oil. Various improved components are discussed in more detail below, such as decreased lignin, decreased phytates, and increased sugars and starch.

The subject invention now provides, for the first time, yellow-seeded, low-fiber canola that also provides a superior, high oleic and low linolenic oil. In addition, the subject invention surprisingly further provides these traits in combination with other valuable traits (such as excellent yield, high protein content, and high oil content (in addition to quality). Generally, the yellow seeds of the subject invention have a considerably thinner seed coat than black and brown ones. The thinner seed coat results in a reduced fiber content in the meal and an associated increase in seed oil and protein content as compared with normal levels of oil and protein. The subject yellow-seeded genotypes generally have higher oil and protein concentrations in their seeds. Furthermore, when edible protein products are made from rapeseed meal the dark color of black seed is a considerable problem. The black-seed coat gives an unpleasant grey color to protein products made from rapeseed meal. Therefore the reduction in seed coat color of the rapeseed of the invention increases protein quality and improves the overall available energy provided by the meals of the subject invention.

Plant lines capable of yielding NATREON-like oil profiles, combined with the yellow seed trait and associated improvements in the resulting meal, have not previously been achieved. Thus, the subject invention advantageously provides not only yellow-seeded canola lines, but yellow-seeded canola lines having advantageous NATREON-like oil profiles. Further surprising is that these advantageous oil profiles could be achieved, with yellow seeds, while providing excellent yield, protein quality, and other advantageous qualities.

Thus, the subject invention provides, for the first time, canola seeds having two highly useful components: an excellent oil component, and a highly nutritional meal component. Various aspects of these components are described in more detail below.

In some specific embodiments, the subject invention provides yellow-seeded varieties of *Brassica napus* having advantageous (naturally stable (not hydrogenate) high oleic, low linolenic) oil profiles, wherein some of the varieties are selected from DN03-3743, DN03-3745, DN03-3746, DN03-3747, DN03-3748, DN03-3749, DN03-3744, and DN03-4169. Canola lines of the subject invention have been stabilized to produce yellow seeds having a linolenic acid content of less than 3% and an oleic acid content of 68% or more relative to total fatty acid content. In accordance with the present invention, a substantially uniform assemblage of rapeseed can be produced. Such seed can be used to produce a substantially uniform field of rape plants.

As shown herein, these are the minimum requirements for the oil, and even better results have been achieved. For example, in preferred embodiments, seed (of the subject invention) obtained from plants (of the subject invention) yield oil having over 70%, over 71%, over 71.5%, and over 72% (and in some cases, up to 72.4% and 72.7%) oleic acid, while having linolenic acid content of less than 2.4%, less than 2%, less than 1.9%, less than 1.8%, and down to 1.7%. These advantageous oil profiles have been achieved while retaining various other valuable characteristics in the meal component, as discussed above and in more detail below.

Still further, oils having these profiles have been obtained from plants having a seed color rating of less than 2, less than 1, and as low as 1. Unless otherwise indicated, as reported herein, the seed color rating or "seed color" is generally scored on a 1-5 scale based on seeds obtained from healthy plants at or near complete seed maturity. "1" signifies a good yellow color. "2" signifies mainly yellow with some brown. "3" indicates a mixture of brown and yellow. "4" and "5" signify brown and black, respectively. Whiteness index (WI) scores are also provided in Table 2 and are described in more detail below in the Examples. Yellow-seeded parent lines YN97-262 and 9592 have whiteness index scores of −34.6 and −33.2, respectively, and seed color scores of 1. Black-seeded NATREON lines, Nex 715 and Nex 705 have whiteness index scores of −0.2 and −4.4, respectively, and seed color scores of 4. Black-seeded comparison lines 46A65 and Q2 have whiteness index scores of 0.3 and −3.9, respectively, and seed color scores of 5. The exemplified 7 "DN03" yellow-seeded-NATREON lines have whiteness index scores between −22.6 and −36.2, and a seed color score of 1 to 2. Thus, yellowness of the subject seeds can also be described in terms of a percentage or other ratio as compared to any of these control or check lines.

TABLE 2

Mean agronomic and quality data BC$_1$F$_6$ progenies and checks from a replicated yield trial carried out at AAFC-Saskatoon site in Year 3.

| ID (Average) | DTF | DTM | Ht | LDG (1-5) | sdwt | Yield kg/ha | % of avg. of 46A65 &Q2 | BLk | Avg. of nearest Westars | C18:1 | C18:2 |
|---|---|---|---|---|---|---|---|---|---|---|---|
| DN03-3743 | 47 | 88 | 104 | 1 | 2.9 | 1075 | 70 | 1.00 | 2.05 | 72.4 | 16.2 |
| DN03-3744 | 46 | 88 | 107 | 1 | 3.4 | 981 | 70 | 0.28 | 2.05 | 71.8 | 17.1 |
| DN03-3745 | 48 | 88 | 105 | 1 | 3.1 | 1064 | 69 | 0.95 | 2.04 | 71.3 | 17.1 |
| DN03-3746 | 48 | 89 | 101 | 1 | 3.0 | 1221 | 80 | 0.88 | 2.04 | 72.1 | 16.7 |
| DN03-3747 | 44 | 87 | 94 | 1 | 3.2 | 1195 | 78 | 1.20 | 2.80 | 72.2 | 17.0 |
| DN03-3748 | 47 | 90 | 100 | 1 | 3.3 | 954 | 62 | 0.61 | 2.80 | 72.0 | 17.0 |
| DN03-3749 | 47 | 90 | 98 | 1 | 3.4 | 942 | 61 | 0.84 | 2.55 | 72.7 | 16.3 |

TABLE 2-continued

Mean agronomic and quality data BC₁F₆ progenies and checks from a replicated yield trial carried out at AAFC-Saskatoon site in Year 3.

| Nex 715 | 45 | 87 | 102 | 1 | 3.2 | 1300 | 85 | 0.23 | 2.55 | 77.2 | 12.3 |
|---|---|---|---|---|---|---|---|---|---|---|---|
| Nex 705 | 46 | 89 | 95 | 1 | 3.5 | 1729 | 112 | 1.08 | 2.60 | 76.6 | 13.0 |
| DN99-6738 Arg | 50 | 88 | 107 | 1 | 2.9 | 1535 | 100 | 0.15 | 2.60 | 75.0 | 13.9 |
| DN99-6738-GH | 51 | 89 | 104 | 1 | 2.7 | 1464 | 95 | — | — | 75.4 | 13.5 |
| YN97-262 | 46 | 89 | 98 | 1 | 3.5 | 1240 | 80 | 1.47 | 2.89 | 65.7 | 18.9 |
| YN9592 | 46 | 86 | 104 | 1 | 3.0 | 992 | 65 | 1.89 | 2.89 | 55.6 | 22.3 |
| 46A65 | 42 | 85 | 93 | 1 | 2.5 | 1436 | 94 | 0.30 | 2.65 | 66.9 | 17.7 |
| Q2 | 46 | 87 | 101 | 1 | 2.9 | 1637 | 106 | 0.15 | 2.65 | 66.4 | 17.0 |
| Grand Mean | 46 | 88 | 101 | 1 | | 1255 | | | | | |
| CV | 4.0 | 0.7 | 6 | — | | 16 | | | | | |
| LSD | 2.0 | 0.7 | 7 | — | | 216 | | | | | |
| SED | 1.5 | 0.5 | 5 | — | | 165 | | | | | |

| ID (Average) | C18:3 | % Sat | % Oil | Glucs | Seed color (1-5) | WI | ADF | % Red | ADL | % Red | NDF | % Red |
|---|---|---|---|---|---|---|---|---|---|---|---|---|
| DN03-3743 | 1.9 | 7.0 | 44.30 | 13.00 | 1.0 | -33.4 | 8.3 | 43.0 | 1.2 | 83.0 | 16.1 | 32 |
| DN03-3744 | 1.9 | 6.7 | 45.41 | 12.20 | 2.0 | -22.6 | 8.2 | 43.0 | 1.3 | 81.0 | 1.1 | 29 |
| DN03-3745 | 2.3 | 6.8 | 44.33 | 12.30 | 1.5 | -35.8 | 8.2 | 43.0 | 1.2 | 85.0 | 16.4 | 31 |
| DN03-3746 | 1.8 | 6.8 | 44.48 | 11.80 | 1.0 | -36.2 | 8.2 | 43.0 | 1.2 | 83.0 | 16.3 | 29 |
| DN03-3747 | 1.7 | 6.6 | 44.91 | 11.50 | 1.0 | -35.8 | 8.1 | 44.0 | 1.3 | 84.0 | 15.7 | 28 |
| DN03-3748 | 1.8 | 6.6 | 44.22 | 11.50 | 1.5 | -35.1 | 7.5 | 48.0 | 1.2 | 86.0 | 16.4 | 35 |
| DN03-3749 | 1.8 | 6.7 | 43.52 | 11.20 | 1.5 | -34.8 | 7.7 | 47.0 | 1.0 | 83.0 | 16.0 | 37 |
| Nex 715 | 1.8 | 6.4 | 42.79 | 10.50 | 4.0 | -0.2 | 15.2 | -5.0 | 5.3 | -6.0 | 20.8 | -1 |
| Nex 705 | 1.9 | 6.4 | 47.84 | 11.10 | 4.0 | -4.4 | 11.3 | 21.0 | 2.9 | 44.0 | 17.5 | 12 |
| DN99-6738 Arg | 1.8 | 6.9 | 45.73 | 10.60 | 4.0 | -7.5 | 10.0 | 31.0 | 1.9 | 57.0 | 15.6 | 23 |
| DN99-6738-GH | 1.8 | 7.0 | 45.84 | 10.40 | 4.0 | -9.9 | 9.5 | 34.0 | 2.0 | 60.0 | 16.1 | 23 |
| YN97-262 | 5.9 | 7.2 | 47.29 | 16.90 | 1.0 | -34.6 | 6.9 | 52.0 | 1.2 | 86.0 | 16.5 | 40 |
| YN9592 | 12.9 | 6.8 | 42.44 | 12.50 | 1.0 | -33.2 | 7.0 | 48.0 | 1.0 | 81.0 | 15.9 | 35 |
| 46A65 | 6.1 | 7.0 | 44.21 | 14.70 | 5.0 | 0.3 | 13.0 | 5.0 | 4.9 | 6.0 | 19.6 | 1 |
| Q2 | 7.2 | 7.0 | 43.79 | 13.70 | 5.0 | -3.9 | 10.5 | 22.0 | 3.3 | 36.0 | 18.6 | 16 |
| Grand Mean | | | 44.65 | | | | | | | | | |
| CV | | | 1.3 | | | | | | | | | |
| LSD | | | 0.7 | | | | | | | | | |
| SED | | | 0.5 | | | | | | | | | |

1 = erect
5 = flat on ground

The meal component of seeds of the subject invention has high protein, low fiber, low lignin, low glucosinolates, low phytates, and/or low sinapic acid esters (SAEs), for example. Insoluble fiber, lignin, glucosinolates, phytates, and SAEs are antinutritional and impair protein and amino acid digestion. Plants store phosphorous in the form of phytate, so undigested phytate-phosphorous in animal waste is a significant environmental concern.

The subject meal components and animal feeds comprising them are especially good for monogastric animals such as pigs and chickens. While the digestive systems of ruminant animals (such as cattle) are well-suited for fiber and phytate consumption and digestion, those animals do not make good use of the high quality protein component of canola meal because the proteins are rapidly used by rumen bacteria. Thus, reducing fiber, phytate, and SAE components of the subject canola meal can greatly increase the nutritional value of these meals for pigs, chickens, and the like.

As discussed in more detail in the Examples below, the yellow-seeded strains of the subject invention have good yields and produce seeds having much lower acid detergent fiber (ADF), acid detergent lignin (ADL), and neutral detergent fiber (NDF) compared to any of the "control" lines. It should be noted that any of the data points on any of the Tables presented herein can be used to define plants, seeds, and oil of the subject invention. (Any of the exemplified numbers can be used as endpoints to define ranges above, below, or in between any of the exemplified numbers.) Some of these ranges for oil characteristics have been discussed above. The same can also be illustrated for other factors. Lines and seeds of the subject invention can also be defined by combinations of such ranges. For example, the oil characteristics discussed above together with characteristic fiber levels and phytate levels, for example, can be used to define lines and seeds of the subject invention.

Other combinations of such characteristics are also possible. For example, combined total oil and protein content of the seeds is also a useful measure and a unique characteristic of the subject seeds.

As another, more specific example, the eight exemplified "DN03" lines have ADL scores of 1.0, 1.2, 1.3, and 1.7. See Table 2. These scores signify lignin reductions of 81, 83, 84, 85, 86, and 71% (depending on the variety of the subject invention), as compared to Nex 715. Lignin is an especially important component of fiber to reduce for monogastric animal feed because lignin is completely indigestible by such animals. Thus, decreasing lignin in the meal source can greatly increase the metabolizable energy and nutritional value of the meal for such animals.

Furthermore, preferred seeds (and meal) of the subject invention, while providing superior oil as discussed above, also have very desirably low levels of glucosinolates. For example, glucosinolate concentrations can be less than 13 micromoles per gram, less than 12.3, less than 12.2, less than 11.8, less than 11.5, and as low as 11.2 micromoles per gram (measured using standard methodology unless indicated otherwise). Thus, the subject invention includes crushed seeds, wherein said seeds are *Brassica napus* seeds, having an average glucosinolate content (per grams of meal) in the ranges specified above.

Phytate characteristics can also be used to define seeds, plants, and lines or varieties of the subject invention. Phytate for DN03-3746, for example, was determined to be 1.3%, which is lower than all of the "controls" except for Nex 715. Nex 715, however, is a lower-oil line (but is blackleg resistant). See Table 14, below. See also Table 2, which shows about 44.5% oil for DN03-3746 and about 42.8% oil for Nex 715.

In addition to fiber levels and other factors discussed above, metabolizable energy values may be related to sucrose (and other sugar) content in the meal. The subject invention provides canola varieties with high sucrose (and other sugar) content, with improved metabolizable energy and therefore meal value. For example, DN03-3746 has a sucrose content of about 12%, which is considerably higher than 46A65, Nex 705, Nex 715, and Nex 720. DN03-3746 has a glucose content of about 19%, which is considerably higher than Q2, 46A65, Nex 705, Nex 715, Nex 710, and Nex 720. DN03-3746 also has levels of rhamnose, fucose, arabinose (6.1%) and mannose (over 1.8%) that are higher than those for all of Q2, 46A65, Nex 705, Nex 715, Nex 710, and Nex 720. Galactose levels for DN03-3746 of about 4.7% are also higher than those of Nex 705, Nex 715, and Nex 710, and are comparable to those of Nex 720.

Crude protein for DN03-3746 (about 51%) was also higher than that of Q2, 46A65, Nex 705, Nex 715, Nex 710, and Nex 720.

Combined with these aspects of the meal component, the subject invention also includes seeds wherein the oil fraction has an α-linolenic acid content between 1.7% and about 2.3% (or less than this range) relative to the total fatty acid content of said seeds. Further, the oil component can comprise oleic acid from about 71.3% to about 72.7% (or higher). The subject seeds are yellow seeds, having a color score preferably in the range of about 1 to about 2, with corresponding reductions in fiber (including lignin), glucosinolates, phytates, and/or SAE and the like. Preferred ranges for these components of the meal fraction are provided above and elsewhere herein.

One exemplified line of the subject invention (DN03-3746, for example) produces seeds having a seed color score of 1, a whiteness index score of about −36.2, about 44.5% total oil, an oil content comprising about 72% oleic acid and about 1.8% linolenic acid, and a meal component having about 8.2% ADF, about 1.2% ADL, about 16.3% NDF, about 47% protein, and about 1.3% phytate. Not all of these characteristics are needed to define lines and seeds of the subject invention, but additional characteristics can be used to define lines and seeds of the subject invention (such as % sucrose, AME, etc.). The main characteristics are the yellow seed coat and the advantageous (high oleic, low linolenic) oil profiles.

Various combinations of traits can also be identified in, and are exemplified by, the DN04 or "04" lines provided in Examples below. Particularly noteworthy in these Examples for these lines are the yield, % oil, and % protein numbers, in addition to the oil profile and reduced fiber contents. These lines illustrate that the subject invention can be used to provide and obtain various new and unexpected combinations of a wide variety of advantageous canola characteristics and traits.

Advantageous traits of the subject *Brassica napus* lines can be transferred to other types of *Brassica* (through conventional breeding and the like), such as *Brassica rapa*, with the resulting plants producing seeds having yellow seed coats and improved oil content (oleic acid content greater than 68% and linolenic acid content less than 3%). Meals and seeds of the subject invention have a decreased level of seed fiber and other related characteristics.

Thus, the subject invention addresses a need for canola seed lines with improved oil and utilizable protein contents, and decreased fiber content. The invention is drawn to rapeseeds that have the advantageous combination of a superior oil content together with yellow seed coats. There are related aspects of the subject invention, such as the plants that produce such rapeseeds. The subject invention includes not only yellow seeds of canola having NATREON oil profiles, but also plants grown or otherwise produced from such seeds, and tissue cultures of regenerable cells of the subject canola plants. It should also be noted that the exemplified lines were obtained without genetic engineering and without mutagenesis.

The subject invention relates generally to any yellow-seeded canola plant, or yellow seed itself, wherein the seed has NATREON-type oil profiles. In some specific embodiments, the present invention is directed to specific lines as disclosed herein. Seed from two representative lines has been deposited. As part of this disclosure, at least 2500 seeds of DN03-3746 and DN03-4169 have been deposited and made available to the public without restriction (but subject to patent rights), with the American Type Culture Collection (ATCC), Rockville, Md. 20852. The deposits have been designated as ATCC Deposit Nos. PTA-6806 and PTA-6807, respectively, with a deposit date of Jun. 24, 2005. The deposits will be maintained without restriction at the ATCC depository, which is a public depository, for a period of 30 years, or five years after the most recent request, or for the effective life of the patent, whichever is longer, and will be replaced if it becomes nonviable during that period.

The subject invention includes seed of any of the *Brassica napus* varieties disclosed herein. The subject invention also includes *Brassica napus* plants produced by such seed, as well as tissue cultures of regenerable cells of such plants. Also included is a *Brassica napus* plant regenerated from such tissue culture, particularly where said plant is capable of expressing all the morphological and physiological properties of an exemplified variety. Preferred *Brassica napus* plants of the subject invention have the important and/or identifying physiological and morphological characteristics of a plant grown from the deposited seed.

This invention further comprises progeny of such seed and seed possessing the quality traits of interest. This invention further includes processes of making crosses using lines and/or varieties of the subject invention as at least one parent of the progeny of the above-described seeds and oil derived from said seeds.

For example, the subject invention includes an $F_1$ hybrid *Brassica napus* plant having as one or both parents any of the plants exemplified herein. Also within the subject invention is *Brassica napus* seed produced by such $F_1$ hybrids of the subject invention. This invention includes a method for producing an $F_1$ hybrid *Brassica napus* seed by crossing an exemplified plant with a different in-bred parent canola plant and harvesting the resultant hybrid seed. The subject invention includes an exemplified plant that is either a female parent or a male parent.

The exemplified oil and protein levels and profiles can be further improved by crossing the plants of the invention with other lines having high oil and protein levels. Likewise, other characteristics may be improved by careful consideration of the parent plant. Lines of the subject invention are beneficial for crossing the yellow-seed and ideal oil profile traits into other rape or canola lines. These traits can now be transferred into other plants within the same species by conventional plant breeding techniques including cross-pollination and selection of the progeny. Also, the desired traits can be transferred between species using the same convention plant breeding techniques involving pollen transfer and selection. See, e.g., *Brassica crops and wild allies biology and breeding*, edited by S. Tsunada et al., Japan Scientific Press, Tokyo (1980); *Physiological Potentials for Yield Improvement of Annual Oil and Protein Crops*, edited by Diepenbrock and Becker, Blackwell Wissenschafts-Verlag Berlin, Vienna (1995); Canola and Rapeseed, edited by F. Shahidi, Van Nostrand Reinhold, N.Y. (1990); and *Breeding Oilseed Brassicas*, edited by Labana et al., Narosa Publishing House, New Dehli (1993).

Having obtained and produced representative lines of the subject invention, the subject yellow seed coat color and oil traits can now be readily transferred into other plants, including *Brassica campestris* species, by conventional plant breeding techniques and the like. Such conventional techniques include cross-pollination and selection of the progeny. Such techniques can likewise be used to transfer the trait between species. Commercially available *campestris* varieties, for example, include Tobin, Horizon, Colt, and the like. One approach includes, following the interspecific cross, self-pollinating members of the $F_1$ generation to produce $F_2$ seed. Backcrossing can then be conducted to obtain lines exhibiting the desired trait. Additionally, protoplast fusion and nuclear transplant methods can be used to transfer the trait from one species to another. See, generally, "Fusion of Higher Plant Protoplasts" by Albert W. Ruesink, *Methods in Enzymology*, Vol. LVIII, Jakoby and Pastan. (eds). Academic Press, Inc., New York, N.Y. (1979), and the references cited therein; and Carlson et al. (1972), *Proc. Natl. Acad Sci. USA* 69:2292.

The present invention includes varieties of *Brassica napus*, as well as essentially derived varieties that have been essentially derived from at least one of the exemplified varieties. In addition, the present invention includes a plant of at least one of the exemplified varieties, a plant of such an essentially derived variety, and a rape plant regenerated from such plants or tissue (including pollen, seeds, and cells) thereof.

It will be readily apparent that, given one of the subject varieties as a starting point, the particular benefits afforded by this variety can be manipulated in a number of ways by the skilled practitioner without departing from the scope of the present invention. For example, the seed oil profile present in an exemplified variety can be transferred into other agronomically desirable *Brassica napus* varieties by conventional plant breeding techniques involving cross-pollination and selection of the progeny, for example.

Plant cells can be selected that are capable of regeneration such as seeds, microspores, ovules, pollen, vegetative parts, particularly microspores. For the most part, such plant cells can be selected from any variety of *Brassica*, particularly those having desired agronomic traits.

Regeneration techniques are known in the art. One can initially select cells capable of regeneration (e.g., seeds, microspores, ovules, pollen, vegetative parts) from a selected plant or variety. These cells can optionally be subjected to mutagenesis. A plant is then developed from the cells using regeneration, fertilization, and/or growing techniques based on the type of cells (and whether they are mutagenized). Applicable regeneration techniques are known to those in the art; see, for example, Armstrong, C. L., and Green, C. E., *Planta* 164:207-214 (1985); Duncan, D. R. et al., *Planta* 165:322-332 (1985); and, Close, K. R., and Ludeman, L. A., *Plant Science* 52:81-89 (1987).

Such manipulations of plants or seeds, or parts thereof, may lead to the creation of what may be termed "essentially derived" varieties. The International Union for the Protection of New Varieties of Plants (UPOV) has provided the following guideline for determining if a variety has been essentially derived from a protected variety:

[A] variety shall be deemed to be essentially derived from another variety ("the initial variety") when
(i) it is predominantly derived from the initial variety, or from a variety that is itself predominantly derived from the initial variety, while retaining the expression of the essential characteristics that result from the genotype or combination of genotypes of the initial variety;
(ii) it is clearly distinguishable from the initial variety; and
(iii) except for the differences which result from the act of derivation, it conforms to the initial variety in the expression of the essential characteristics that result from the genotype or combination of genotypes of the initial variety.

UPOV, Sixth Meeting with International Organizations, Geneva, Oct. 30, 1992; document prepared by the Office of the Union.

Preferred embodiments of the subject invention include meals wherein said meal comprises canola seed wherein said seed has oil and meal characteristics as discussed above. The subject invention includes hexane-extracted, air-dried canola meal having a novel combination of characteristics as discussed above. The subject invention includes meal produced from the deposited *Brassica napus* seeds, and meal produced from seeds of progeny of said deposited seeds.

As used herein, a "line" is a group of plants that display little or no genetic variation between individuals for at least one trait. Such lines may be created by several generations of self-pollination and selection, or vegetative propagation from a single parent using tissue or cell culture techniques. As used herein, the terms "cultivar" and "variety" are synonymous and refer to a line that is used for commercial production.

"Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercially useful" lines have good plant vigor and high fertility, such that the crop can be produced by farmers using conventional farming equipment, and the oil with the described components can be extracted from the seed using conventional crushing and extraction equipment. To be commercially useful, the yield, as measured by both seed weight, oil content, and total oil produced per acre, is typically within 15% of the average yield of an otherwise comparable commercial canola variety without the premium value traits grown in the same region. "Agronomically elite" lines have desirable agronomic characteristics such as yield, maturity, disease resistance, and standability.

Following is a list of the common names of fatty acids, as used herein, together with their number of carbon atoms and double bonds. Saturated fats have zero double bonds.

TABLE 3

| Name | Number of Carbon Atoms Per Molecule | Number of Double Bonds Per Molecule |
|---|---|---|
| Lauric | 12 | 0 |
| Myristic | 14 | 0 |
| Palmitic | 16 | 0 |
| Palmitoleic | 16 | 1 |
| Stearic | 18 | 0 |
| Oleic* | 18 | 1 |
| Vaccenic** | 18 | 1 |
| Linoleic | 18 | 2 |
| Alpha-Linolenic | 18 | 3 |
| Arachidic | 20 | 0 |
| Eicosenoic | 20 | 1 |
| Behenic | 22 | 0 |
| Erucic | 22 | 1 |
| Lignoceric | 24 | 0 |
| Nervonic | 24 | 1 |

*= double bond at delta-9 position
**= double bond at delta-11 position

"Saturated fatty acid" refers to the combined content of lauric (C12:0), myristic (C:14:0), palmitic (C16:0), stearic (C18:0), arachidic (C20:0), behenic (C22:0), and lignoceric (24:0) acids. "Polyunsaturated fatty acid" refers to the combined content of linoleic and α-linolenic acids. The amount of fatty acids, such as oleic and linolenic acids, that are characteristic of the subject oils are expressed as a percentage of the total fatty acid content of the oil (unless otherwise specified).

"Protein content" is measured as percent of whole dried seed, and different varieties have different characteristic protein contents. Protein content can be determined using various analytical techniques such as NIR and Kjeldahl.

Glucosinolates are measured in micromoles (μm) of total alipathic glucosinolates per gram of air-dried oil-free meal. The level of glucosinolates is somewhat influenced by the sulfur fertility of the soil but is also controlled by the genetic makeup of each variety (and thus can be useful in characterizing varieties).

Unless otherwise indicated, all calculations (for fiber content and the like) were obtained using techniques that are known in the art and accepted in the industry.

The present invention has of necessity been discussed herein by reference to certain specific methods and materials. The enumeration of these methods and materials is merely illustrative and in no way constitutes any limitation on the scope of the present invention. It is to be expected that those skilled in the art may discern and practice variations of or alternatives to the specific teachings provided herein, without departing from the scope of the present invention.

Unless indicated otherwise, the terms "a" and "an" as used herein refer to at least one.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Parent Lines and Year 0

In Year 0, the following parent lines were selected: DAS NATREON *B. napus* Nex 705 (M94S007) and Nex 715 (M97A222), and AAFC yellow-seed lines YN97-262 and 9592. Nex 715 is lower in oil than Nex 710, but Nex 715 has blackleg resistance genes. Quality and agronomic data of these lines was measured for comparative purposes and to track the progress and improvement of subsequent lines.

Nex 705 was used in backcrosses to create the following two progenies: YN97-262/Nex 715//Nex 705 and 9592/Nex715//Nex 705.

To introgress blackleg resistance genes, these progeny were backcrossed with Nex 715 to produce the following two progenies: YN97-262/Nex 705//Nex 715 and 705, 9592/Nex 705//Nex 715.

1235 $BC_1F_1$ plants were grown to produce $BC_1F_2$ seeds.

EXAMPLE 2

Year 1

In Year 1, 1092 $BC_1F_2$ rows were grown in Saskatoon. These comprised of 540 BC1F2 progenies from [9592/Nex705//Nex 705] and [9592/Nex715//Nex 705], and 552 BC1F2 progenies from [YN97-262/Nex 705//Nex 715] and [YN97-262/Nex 715//Nex 705]. 268 BC1F2 progeny rows were also grown from the 9592 crosses, and 252 BC1F2 progeny rows from the YN97-262 crosses.

In addition, 272 BC1F2 progenies rows from the 9592 cross, and 300 BC1F2 progenies from YN97-262 crosses were grown at AAFC site in Saskatoon Each BC1F2 row was replicated twice, and the parents were used as checks every $10^{th}$ row in the nursery.

For the plants grown at the Moon Lake location, rows segregating for yellow-seeded color were identified. All plants in each BC1F2 row were evaluated for seed color in the first replication, and only plants with good yellow color were harvested. In the second replication, only lines that exhibited seed color rating of 3 or better in $1^{st}$ replication were harvested.

For the plants grown in AAFC Saskatoon site, the first replication was combine harvested, and then the seeds were rated for the presence of yellow. Based on this selection, all plants from segregating yellow-seeded rows were harvested from the second replicate, including some rows of parental checks.

For seed obtained from both sites, bulk fatty acid analysis was first conducted on selected BC1F3 plants followed by half-seed fatty acid analysis in plants that exhibited high C18:1 and low C18:3.

EXAMPLE 3

December Year 1 to April Year 2

BC1F3 plants were grown to produce BC1F4 seed in the greenhouse. Seed color selection was carried out, and only 189 BC1F4 plants were selected for Year 2 field evaluation.

The BC1F4 lines were evaluated in a replicated nursery at the Moon Lake site and at the Saskatoon site. Two replications were seeded at each site. 28 lines exhibiting good agronomic characteristics at both sites were selected, and 10 single plants were harvested from each row. Remaining plants from each row were bulked and analyzed for oil and fatty acid profile.

Individual plants were color rated using a scale of 1-5. Plants with a rating of 2 or better were sent for fatty acid analysis. Seven single plants from 3 BC rows were selected and ½-seed analysis was carried out.

The following four true-breeding, yellow, NATREON-type *B. napus* BC1F5 lines were identified: DN02-0548, DN02-0590, DN02-0591, and DN02-0592. Bulk seed samples from these four lines and checks were used to determine the oil and fiber levels. Relative to the black seeded variety Nex 715, the 4 lines had an average of a 34% reduction in acid detergent fiber, a 68% reduction in acid detergent lignin, and a 14% reduction in neutral detergent fiber.

EXAMPLE 4

Winter Year 2 to Year 3

Half-seeding was done in seven BC1F5 lines from DN02-0590, DN02-0591, and DN02-0592. These were grown in a greenhouse in the winter of Years 2-3.

In addition, a BC2F1 cross was produced by crossing BC1F5 plants to a Natreon line DN99-6738 (which has high oil and protein, is R-rated for blackleg, and has a good Natreon profile). The BC2F1 were microspore cultured to produce yellow NATREON-type DH lines evaluated in the nursery in Year 4.

In a replicated yield trial in Year 3, bulk selfed seed of BC1F6 plants was used to assess the agronomic and quality performance of the yellow NATREON-type lines relative to Nexera commercial varieties and WCC/RRC (Western Canadian Canola/Rapeseed Recommending Committee) black-seeded check varieties (Q2 and 46A65).

backcross generations were designated as DN03-3743, DN03-3744, DN03-3745, DN03-3746, DN03-3747, DN03-3748, and DN03-3749. DN03-4169 is another yellow-seeded line produced from 9592/Nex 715/Nex 705 cross. These lines exhibited NATREON-type oil quality and very stable yellow seed color.

Table 2 indicates, for field grown material from these lines, reductions in fiber levels that were achieved, relative to mean of Nex 715 & 46A65.

These lines are stable and uniform after 6 generations of selection. No off-type plants have been exhibited in various evaluations. The most advanced cross with these lines is a BC2F1-derived population that was in stage 1B in the summer of year 4.

These lines with yellow-seeded NATREON-type oil profiles have exhibited commercially valuable characteristics in multi-year evaluations. The true-breeding yellow NATREON-type lines are also valuable material for use in feed, where the value (including monetary) of the reduction in dietary fiber can be readily demonstrated.

Data obtained from these eight lines grown at the Saskatoon site are provided in Table 2. These data include: days to flower (DTF), days to maturity (DTM), height, lodging, seed weight, yield, and blackleg resistance. Also included are percent of C18:1, C18:2, and C18:3 fatty acids, total % saturates, % oil (total oil content) (American Oil Chemists' Society (AOCS) official Method Am 2-92), glucosinolates (AOCS Official Method Ak 1-92 (93)), seed color score, ADF, ADL, and NDF (and the percent reduction of the latter three fiber scores as compared to Nex 715). Table 4 presents data from these six lines grown at the Moon Lake site, in addition to the parental NATREON lines DN99-6738 (A.K.A. NQC02X01). The % protein for the lines of the subject invention is also noteworthy.

TABLE 4

Mean agronomic and quality data BC$_1$F$_6$ progenies and checks from a replicated yield trial carried out at Moon Lake in Year 3

| Name | Source | Pedigree | DTF | DTM | HGT | LDG | C18:1 | C18:2 | C18:3 | % Sats | % oil | % Protein | Color |
|---|---|---|---|---|---|---|---|---|---|---|---|---|---|
| DN033743 | DN02-0591 F4 | YN97-262/M97A222//M94S007 | 54 | 88 | 110 | 1.0 | 72.6 | 16.1 | 2.0 | 6.8 | 45.7 | 47.3 | 2 |
| DN033744 | DN02-0591 F4 | YN97-262/M97A222//M94S007 | 52 | 87 | 110 | 1.5 | 73.5 | 16.4 | 1.6 | 6.2 | 46.9 | 47.2 | 2.5 |
| DN033745 | DN02-0590 F4 | YN97-262/M97A222//M94S007 | 50 | 87 | 103 | 1.5 | 72.1 | 16.5 | 2.1 | 6.9 | 45.9 | 47.3 | 1.5 |
| DN033746 | DN02-0590 F4 | YN97-262/M97A222//M94S007 | 52 | 89 | 110 | 1.0 | 72.7 | 16.8 | 1.7 | 6.5 | 45.0 | 47.0 | 1.5 |
| DN033747 | DN02-0590 F4 | YN97-262/M97A222//M94S007 | 51 | 87 | 105 | 1.5 | 72.9 | 16.6 | 1.6 | 6.6 | 47.3 | 47.6 | 2 |
| DN033748 | DN02-0592 F4 | YN97-262/M97A222//M94S007 | 52 | 89 | 108 | 1.5 | 71.4 | 17.8 | 1.8 | 6.4 | 43.1 | 45.1 | 1.5 |
| DN033749 | DN02-0592 F4 | YN97-262/M97A222//M94S007 | 51 | 88 | 108 | 2.0 | 72.2 | 17.2 | 1.9 | 6.4 | 44.0 | 45.9 | 1.5 |
| DN034169 | DN02-0548 F4 | 9592/M97A222//M94S007 | 51 | 88 | 100 | 2.0 | 72.5 | 15.9 | 2.4 | 6.7 | 43.4 | 46.0 | 1.5 |
| 46A65 | | | 45 | 85 | 103 | 1.5 | 66.3 | 17.8 | 6.6 | 7.1 | 48.0 | 42.8 | 5 |
| 9592 | | | 52 | 86 | 103 | 1.5 | 57.7 | 22.0 | 11.0 | 7.0 | 42.7 | 46.5 | 2 |
| NQC02X01-ARG | | | 54 | 88 | 110 | 1.5 | 75.6 | 13.6 | 1.6 | 7.0 | 46.8 | 46.1 | 4.5 |
| NQC02X01-GH | | | 55 | 88 | 100 | 1.5 | 75.5 | 13.8 | 1.5 | 6.9 | 47.3 | 46.2 | 4.5 |
| Q2 | | | 52 | 86 | 108 | 2.5 | 66.8 | 17.0 | 7.0 | 7.0 | 47.4 | 45.4 | 5 |
| YN97262 | | | 54 | 87 | 110 | 1.5 | 67.0 | 18.0 | 5.6 | 7.2 | 49.1 | 47.6 | 2 |

EXAMPLE 5

Development of Further Lines

The 7 BC1F6 lines developed from the cross of YN97-262/Nex 715//Nex 705 through traditional backcrossing methods, followed by reselection of yellow & NATREON quality in

EXAMPLE 6

Protocol for Determination of Metabolizable Energy and Chemical Composition of Yellow-Seeded Canola Meal, and Performance of Broiler Chickens Amino acid digestibility (ileal) was determined with commercial broiler cockerels housed in cages. Chicks were fed commercial meal diet from 1 to 27 days of age and transferred to a treatment diet containing 0 or 40% of the Canola meal.

Test meal was added to the basal diet at the expense of the diet as a whole. After an adjustment period of 7 days, the birds were sacrificed by cervical dislocation and the contents of the distal ileum (the section between 12 cm and 2 cm anterior to the ileal cecal junction) were collected and frozen for analysis at a later period. Each diet was fed to 4 groups of 2 birds each. Ileal contents were freeze-dried, ground, and mixed thoroughly before analysis for gross nitrogen (AOAC, 1980), amino acid content, and acid insoluble ash (Newkirk et al., 2003).

Nitrogen-corrected apparent metabolizable energy (AMEn) was determined in the same trial, but feces were collected daily for the last 3 days of the trial. The feces were frozen immediately after each collection. The frozen feces were dried at 50° C. in a forced air oven, and then pooled with feces from other collections of the same rep and treatment. The samples were ground (1 mm grind) and analyzed for gross energy, acid insoluble ash, and nitrogen.

AMEn and illeal apparent amino acid digestibility were calculated using the method reported by Newkirk et al. (2003). Data were collected as follows:

TABLE 5

| Date | Bird Age | Detail |
|---|---|---|
| Feb 13/Year 3 | 0 | Place birds, feed commercial starter diet |
| March 13/Year 3 | 28 | Record bird weights, place on experimental diet |
| March 17/Year 3 | 32 | Remove feces, place plastic under trays pm fecal collection |
| March 18/Year 3 | 33 | Collect feces AM & PM |
| March 19/Year 3 | 34 | Collect feces, weight feed and birds, collect ileal samples (AM) |

Further details of the studies were as follows:

1. Feeding Study: February Year 3-May Year 3
   a. Treatments: 6 NATREON varieties (Nex 705, Nex 710, Nex 715, Nex 720, CMI#1-transgenic and CMI#1-Null) from Dow AgroSciences plus 1 reference diet (yellow-seeded line DN03-3746) will used in the project. 10 kg of seed of each varieties will be crushed by POS to obtain 5-kg oil free meal. Each of the treatment will be assigned randomly to pens and blocked with pen.
   b. Experimental design: a completely randomized block design with 6 replications will be used. One way analysis of variance with mean separation will be used for data analysis. Multivariate regression analysis will be applied to chemical composition and metabolisable energy data.
   c. Bird Class: bird type: broiler; strain: Ross 308; sex: male; source: Wynard; 84 birds
   d. Temperature: Standard curve: Day 0-35° C. by Day 34-22° C.
   e. Lighting: 50 lux light was maintained on a 23 hour light:1 hour dark cycle, for days 1-34
   f. Feed and Water: ad libitum; feeders were kept at a moderate level; birds were fed often; the amount of feed spillage was especially minimized during fecal collection period.
   g. Litter management: Removed as necessary, on Day 31 remove all feces and place plastic sheets under the birds for fecal collection.
   h. Feed requirements: Birds aged 0-26 days consumed 2 kg/bird commercial starter; birds aged 27-34 days consumed 1 kg/bird experimental diet
   i. Meal requirements: 6 reps*2 birds/rep*1 kg/bird feed*40% meal=4.8 kg for diet, 200 g for analysis=5 kg/meal
   j. Dietary specifications:

TABLE 6

Experimental Diets

| | Ingredient | Reference diet % | Test Diet % |
|---|---|---|---|
| Basal premix | Corn | 91.89 | 53.35 |
| | Canola oil | 3.46 | 2.0 |
| Micronutrient premix | Celite | 1.0 | 1.0 |
| | vitamin/mineral | 0.5 | 0.5 |
| | Choline Cl | 0.1 | 0.1 |
| | Dical | 1.81 | 1.81 |
| | Limestone | .84 | .84 |
| | Salt | .40 | .40 |
| Test ingredient | Canola meal | | 40.00 |
| Calculated nutrient content | | % | |
| CP | | 7.7 | 18.92 |
| $AME_n$ (kcal/kg) | | 3380 | 2755 |
| Available P | | .42 | .5 |
| Ca | | .74 | 1.0 |
| Lysine | | .24 | .942 |
| Met + Cys | | .34 | .87 |

TABLE 7

Micro Nutrient Premix

| Ingredient | % | Kg |
|---|---|---|
| Dical | 35.14 | 2.460 |
| Celite3 | 19.42 | 1.358 |
| Limestone | 16.31 | 1.142 |
| Vitamin mineral premix | 9.71 | 0.680 |
| Salt | 7.77 | 0.544 |
| Choline | 1.94 | 0.136 |
| Total | | 7.000 |

TABLE 8

Basal Premix (2, 40 kg batches intermixed)

| Ingredient | % | Kg |
|---|---|---|
| Corn | 96.35 | 38.54 |
| Canola Oil | 3.65 | 1.46 |
| Total | 100 | 40 |

TABLE 9

Diet composition (12 kg; 12 birds *1 kg/bird)

| | Reference diet | | Test Diet | |
|---|---|---|---|---|
| Ingredient | % | Kg | % | kg |
| Basal premix | 94.85 | 14.22 | 54.85 | 6.58 |
| Micronutrient premix | 5.15 | .773 | 5.15 | .618 |
| Test ingredient | 0 | 0 | 40 | 4.8 |
| Total | 100 | 15 | 100 | 12 |

TABLE 10

Analyses to be conducted on meals (DAA to conduct)

| Energy contributing | Energy diluting |
|---|---|
| Protein | Total dietary fiber (including soluble and insoluble fiber) |
| Amino acids | NDF |
| Ether extract | ADF |
| Sucrose | Ash |
| Oligosaccharides | Moisture |
| Starch | Lignin (ADL, NDL) |

Data Reporting:

Data was obtained by mid-April Year 3 and analysis done by mid-May Year 3 except for the detailed analysis of total dietary fiber fractions and oligosaccharides which were not completed until August 3.

2. Germplasm Screening to select lines for use in nutrient retention tests:

40 g of seed from 37 NATREON Breeding lines were assessed for chemical composition of the meal using the parameters identified herein. Based on the results obtained, lines were identified for use in broiler chicken nutrient retention testing.

The seed was solvent extracted with hexane at POS Pilot Plant in Saskatoon, SK. The air-desolventized meal was provided to the University of Saskatchewan for chemical analysis.

The meal was ground through a 1 mm screen prior to chemical analysis. Each sample was analysed in duplicate for the chemical compositions (except amino acids) shown in Table 10.

Crude protein was determined by combustion using the Leco method. Ether extract was determined using the AOAC (1990) method with a Labconco Model 35001 Goldfisch extractor. The meal was extracted for 4 hours extraction using diethyl ether.

Sucrose, free glucose, stachyose, and raffinose were analysed by GLC using a DB1701 column and TMSI derivitization. Oligosacharides (dp 3-10) were analysed by HPLC by gel permeation and refractive index detection. Starch was determined by the method of Salmonsson, A. C. et al, (1984, Swed. J. Agric. Res., 14:111-117).

Soluble, insoluble, and total dietary fiber were determined using the method of Mongeau and Brassard (1990, Cereal Foods World 35:319-322). The soluble and insoluble fiber fractions were subjected to total sugar analysis (Englyst, H. N. and Hudson, G. J., 1987 Animal Feed Sci. and Tech., 23:27-42). Neutral detergent fiber (NDF), acid detergent fiber (ADF) and NDF-lignin and ADF-lignin determination was conducted using the method of Van Soest, et al. (1991. J. Dairy Sci. 74:3583-3597).

Ash and moisture content (another energy diluter) were determined using the method of AOAC, (1990 Official Methods of Analysis. 15$^{th}$ ed. Association of Official Analytical Chemists. Washington, D.C.).

3. May Year 3 to November Year 3:
Carried out seed increase of 10-15 lines to produce 10 kg seed per variety and completed the detailed analysis of total dietary fiber fractions and oligosaccharides of initial 6 varieties.

4. November Year 3-February Year 4
a. Obtained 5-kg oil free meal from each of the 10-15 varieties
b. Carried out a trial to assess broiler chicken nutrient retention Treatments:

15 NATREON lines including the Yellow-seeded line DN03-3746, 4 Dow AgroSciences commercial controls from the first trial (Nex 705, Nex 710, Nex 715 and Nex 720) and 1 reference diet were used in the project. 10 kg of seed of each varieties was crushed by POS to obtain 5-kg oil free meal. Each of the treatment was assigned randomly to pens and blocked with pen.

Experimental Design:

a completely randomized block design with 6 replications was used. Due to limited space in the battery cages, 3 replications were conducted in bird trial #1 and 3 remaining replications were conducted in trial 2. Data was analysed by blocking within trial. One-way analysis of variance with mean separation was used for data analysis. Multivariate regression analysis was applied to chemical composition and metabolisable energy data.

Data Reporting:

Data was reported mid-January Year 4 and analysis done by mid-February Year 4.

5. November Year 3-November Year 4

Development of Chemical Predictors of Metabolisable Energy in Canola Meal.

The meal from the 15 lines increased during the summer of Year 3 had undergone chemical analysis, and data was regressed against the metabolisable energy of the meals to determine the relationship between measured components and metabolisable energy. Multivariate approaches was used, including PCA, to develop predictive equations. Resulting regression equations was then used to determine the best ways of selecting for future higher valued varieties of canola meal.

Oil free, air desolventized meal was ground through a 1 mm screen prior to chemical analysis. Each sample was analysed in duplicate for the chemical composition (protein, ether extract, sucrose, oligosaccharides, starch, total dietary fiber (soluble and insoluble), NDF, ADF, ash, moisture and lignin (ADL and NDL) except amino acids). Crude protein was determined by combustion using the Leco method. Ether extract determination was by the AOAC (1990) method a Labconco Model 35001 Goldfisch extractor. The meal was extracted for 4 hours using diethyl ether. Sucrose, free glucose, stachyose and raffinose was analysed by GLC using a DB1701 column and TMSI derivitization. Oligosacharides (dp 3-10) analysis was done by HPLC by gel permeation and refractive index detection. Determination of starch was by the method of Salmonsson, A. C., O. Theander, and E. Westerlund (1984, Swed. J. Agric. Res., 14:111-117). Soluble, insoluble and Total dietary fiber were determined using the method of Mongeau and Brassard (1990, Cereal Foods World 35:319-322). The soluble and insoluble fiber fractions were subjected to total sugar analysis (Englyst, H. N.; Hudson, G. J., 1987 Animal Feed Sci. and Tech., 23:27-42). Neutral detergent fiber (NDF), acid detergent fiber (ADF) and NDF-lignin and ADF-lignin analyses were conducted using the method of Van Soest, T. J., J. B. Robertson, B. A. Lewis (1991. J. Dairy Sci. 74:3583-3597). Ash and moisture content analyses were determined using the method of AOAC, (1990 Official Methods of Analysis. 15$^{th}$ ed. Association of Official Analytical Chemists. Washington, D.C.).

Data Reporting:

Data was obtained by mid-December Year 4.

EXAMPLE 7

Results and Determination of Digestibility (Apparent Metabolizable Energy and Amino Acid Utilization) of Canola Meal by Broiler Chickens, and Chemical Characterization of the Canola Meal The subject Example discusses the results of measuring the metabolizable energy and amino acid digestibility, by broiler chickens, of special varieties of canola. These samples were also assayed for components that can influence energy utilization. The chemical analyses of these canola samples is also related to digestibility data. Further, this Example discusses chemical characteristics that predict the AME of meals for broiler chickens.

Apparent Metabolizable Energy.

One yellow-seeded line of the subject invention, DN03-3746, was compared to other "check" lines. The measurements for nitrogen-corrected apparent metabolizable energy (AME) are shown in Table 11. As seen in Table 11 (and in Table 12), the AME of the tested yellow-seeded variety, DN03-3746 is superior to that of Nex 705, Nex 715, Q2 (Check 1), and 46A65 (Check 2). Again, only one yellow seeded line of the subject invention was tested; further testing of the other lines of the subject invention is expected to show further improvements in AME.

TABLE 11

Nitrogen corrected apparent metabolizable energy (AMEn) on an as-is basis and dry-matter basis (kcal/g), and apparent ileal protein digestibility (in broiler chickens) of protein in canola varieties.

| Sample | AMEn as-is | AMEn DM | Ileal Prot dig |
|---|---|---|---|
| #16 - Nex 705 | 1626 | 1750 | 75.2 |
| #17 - Nex 715 | 1609 | 1733 | 75.5 |
| #18 - Nex 710 | 1852 | 1988 | 79.2 |
| #19 - Nex 720 | 1806 | 1934 | 79.5 |
| #20 - DN03-3746 | 1794 | 1918 | 74.9 |
| #21 - Check 1 | 1685 | 1810 | 74.6 |
| #22 - Check 2 | 1709 | 1836 | 73.8 |
| #23 - Nex 710 Transgenic | 1987 | 2123 | 80.4 |
| #24 - Nex 710 Null Transgenic | 1783 | 1907 | 79.0 |
| SEM | 16.4 | 17.8 | 0.24 |
| Range | 1600-1994 | 1732-2154 | 73.8-80.4 |

TABLE 12

Digestibility and chemical analyses of canola meal samples shown on a dry matter basis

| Sample ID | % DM | AME[1] (kcal/kg) | AME[2] (kcal/kg) | % Ileal CP digest. | % total digest. aa content[3] | Average aa digest. coefficient[4] | % CP | % Ash | % EE | % Starch | % Sucrose | % Phytate |
|---|---|---|---|---|---|---|---|---|---|---|---|---|
| Nex 705 | 92.88 | 1750 | 1625 | 75.2 | 28.58 | 0.792 | 48.91 | 6.33 | 1.42 | 0.65 | 6.79 | 1.31 |
| Nex 715 | 92.88 | 1733 | 1637 | 75.5 | 29.14 | 0.809 | 46.96 | 5.48 | 1.08 | 0.91 | 9.68 | 1.12 |
| Nex 710 | 93.16 | 1988 | 1865 | 79.2 | 31.01 | 0.838 | 48.65 | 5.81 | 1.39 | 0.69 | 13.22 | 1.36 |
| Nex 720 | 92.94 | 1943 | 1843 | 79.5 | 30.39 | 0.831 | 49.43 | 5.89 | 1.14 | 0.46 | 9.14 | 1.93 |
| DN03-3746 | 93.56 | 1918 | 1813 | 74.9 | 30.54 | 0.770 | 50.95 | 6.38 | 1.19 | 1.03 | 11.98 | 1.30 |
| Check 1 | 93.08 | 1810 | 1693 | 74.6 | 27.63 | 0.813 | 44.85 | 6.20 | 1.32 | 0.32 | 12.87 | 1.48 |
| Check 2 | 93.06 | 1836 | 1768 | 73.8 | 27.68 | 0.767 | 47.97 | 5.76 | 0.77 | 0.21 | 10.32 | 1.73 |
| Nex 710 Transgenic | 93.61 | 2123 | 2020 | 80.4 | 35.49 | 0.851 | 52.20 | 7.29 | 1.17 | 0.15 | 15.13 | 1.89 |
| Nex 710 Null Transgenic | 93.38 | 1910 | 1814 | 79.0 | 33.73 | 0.835 | 52.38 | 7.28 | 1.09 | 0.21 | 15.19 | 2.03 |
| SEM | | 17.6 | | 0.24 | | | | | | | | |
| P Value | | 0.0005 | | 0.0001 | | | | | | | | |
| Mean | | 1789 | | 30.13 | 0.81 | 48.9 | 6.25 | 1.32 | 0.62 | 10.5 | 1.60 | |
| Standard Deviation | | 112.9 | | 2.095 | 0.02 | 2.15 | 0.51 | 0.32 | 0.24 | 2.20 | 0.30 | |
| Minimum | | 1625 | | 26.51 | 0.77 | 44.7 | 5.48 | 0.77 | 0.15 | 6.79 | 1.12 | |
| Maximum | | 2020 | | 35.49 | 0.85 | 52.6 | 7.29 | 2.44 | 1.03 | 15.19 | 2.21 | |

[1] AME on a dry matter basis.
[2] AME on a dry matter basis and corrected to zero percent fat.
[3] Sum of amino acid levels x amino acid digestibility coefficients.
[4] Average of amino acid digestibility coefficients.

Protein and Amino Acid Digestibility.

The effects of canola meal sample on ileal protein digestibility are also shown in Tables 11 and 12. As shown in Tables 11 and 12, the ileal protein digestibility (in broiler chickens) of the DN03-3746 variety is better than that of Q2 and 46A65.

Chemical Analyses.

Results of chemical analyses are found in Tables 12 and 13. In Table 12, the categories tested and compared for DN03-3746 include percent dry matter, AME, protein digestibility and average amino acid digestibility coefficient for all samples. Also included in Table 12 are the crude protein contents, ash content (ash is another energy-diluting component), ether extract (EE—an energy-contributing component), starch, sucrose, and phytate contents. Table 13 includes total dietary fiber (TDF), insoluble TDF (TDF-I), soluble TDF (TDF-S), acid detergent fiber (ADF), acid detergent lignin (ADL), neutral detergent fiber (NDF), neutral detergent insoluble nitrogen (NDIN) and gross energy (GE). Also indicated in Table 13 are amounts of various types of sugars.

desirable, as insoluble nitrogen cannot be used nutritionally (and ties up nitrogen that could otherwise be used by the animal that consumes the meal). Also advantageously, the sugar contents are relatively high. Crude protein for DN03-3746 was also higher than all the check/control lines.

Table 14 shows digestibility and chemical analyses of additional sugars, sinapines, and the like. DN03-3746 has advantageously low levels of sinapine and phytate, and high GE and percentage inositol.

TABLE 13

Further digestibility and chemical analyses of canola meal samples shown on a dry matter basis

| Sample ID | % TDF | % TDF-I | % TDF-S | % ADF | % ADL | % NDF | % NDIN | GE (kcal/kg) | % Rham | % Fucose | % Arab | % Xylose | % Mann | % Galact | % Glucose |
|---|---|---|---|---|---|---|---|---|---|---|---|---|---|---|---|
| Nex 705 | 33.30 | 32.18 | 4.23 | 17.12 | 4.91 | 31.66 | 10.38 | 4745 | 0.300 | 0.236 | 5.198 | 2.009 | 1.291 | 3.983 | 13.713 |
| Nex 715 | 35.96 | 32.94 | 3.93 | 19.89 | 7.54 | 30.88 | 9.19 | 4765 | 0.282 | 0.243 | 5.423 | 2.028 | 1.430 | 4.368 | 15.864 |
| Nex 710 | 32.47 | 29.96 | 5.35 | 15.84 | 3.89 | 29.19 | 8.85 | 4765 | 0.263 | 0.247 | 5.245 | 2.140 | 1.614 | 4.212 | 16.936 |
| Nex 720 | 32.73 | 32.59 | 3.69 | 20.31 | 7.64 | 30.47 | 8.50 | 4790 | 0.348 | 0.282 | 4.903 | 2.250 | 1.399 | 4.716 | 15.866 |
| DN03-3746 | 26.55 | 24.91 | 4.37 | 10.32 | 1.16 | 21.16 | 5.97 | 4769 | 0.381 | 0.315 | 6.105 | 2.679 | 1.841 | 4.696 | 18.810 |
| Check 1 | 33.42 | 32.95 | 5.73 | 18.80 | 6.30 | 30.68 | 9.67 | 4727 | 0.329 | 0.244 | 5.036 | 2.258 | 1.561 | 4.963 | 17.625 |
| Check 2 | 32.95 | 32.57 | 4.16 | 19.66 | 7.87 | 30.47 | 8.84 | 4788 | 0.312 | 0.232 | 5.143 | 2.148 | 1.516 | 4.929 | 15.992 |
| Nex 710 Transgenic | 28.77 | 27.73 | 4.02 | 14.18 | 3.92 | 25.32 | 6.03 | 4735 | 0.288 | 0.240 | 5.001 | 2.104 | 1.720 | 4.082 | 16.882 |
| Nex 710 Null Transgenic | 27.95 | 27.20 | 4.58 | 14.30 | 3.51 | 24.86 | 6.26 | 4740 | 0.237 | 0.201 | 4.146 | 1.788 | 2.139 | 3.035 | 14.213 |
| Mean | 32.51 | 30.73 | 4.70 | 17.06 | 5.14 | 29.00 | 8.665 | 4750 | 0.315 | 0.262 | 5.533 | 2.227 | 1.533 | 4.417 | 15.993 |
| Standard Deviation | 2.546 | 2.489 | 0.961 | 2.934 | 2.322 | 2.969 | 1.272 | 48.8 | 0.0373 | 0.0410 | 0.6312 | 1.533 | 0.1903 | 0.4228 | 1.5968 |
| Minimum | 26.55 | 24.91 | 2.65 | 10.32 | 1.16 | 21.16 | 5.97 | 4621 | 0.237 | 0.201 | 4.146 | 1.788 | 1.264 | 3.035 | 13.537 |
| Maximum | 38.59 | 37.22 | 6.13 | 23.72 | 10.47 | 36.50 | 10.91 | 4821 | 0.381 | 0.412 | 7.111 | 2.689 | 2.139 | 5.003 | 18.810 |

As can be seen on Table 13, total dietary fiber for DN03-3746 was very low, as was insoluble fiber. Insoluble fiber is very undesirable in animal feed and meal. ADF, ADL, and NDF contents for this line are also relatively very low. Insoluble nitrogen (NDIN) is also relatively quite low. This is

TABLE 14

Digestibility and chemical analyses of canola meal samples shown on a dry matter basis.

| Sample ID | Inositol (%) | Raffinose (%) | Stachyose (%) | Sinapic acid (%) | Sinapine (%) | Phytate (%) | GE (kcal/kg) |
|---|---|---|---|---|---|---|---|
| Nex 705 | 0.0651 | 0.1051 | 0.0216 | 0.0239 | 0.826 | 1.38 | 4745 |
| Nex 715 | 0.0834 | 0.1352 | 0.0052 | 0.0183 | 0.725 | 1.13 | 4765 |
| Nex 710 | 0.0890 | 0.2067 | 0.0126 | 0.0230 | 0.870 | 1.43 | 4765 |
| Nex 720 | 0.0828 | 0.1520 | 0.0057 | 0.0182 | 0.702 | 2.02 | 4790 |
| DN033746 | 0.1240 | 0.1666 | 0.0000 | 0.0237 | 0.684 | 1.33 | 4769 |
| Check 1 | 0.0857 | 0.3045 | 0.0000 | 0.0225 | 0.778 | 1.52 | 4727 |
| Check 2 | 0.0867 | 0.2308 | 0.0000 | 0.0269 | 1.003 | 1.77 | 4788 |
| Nex710Null Transgenic | 0.0509 | 0.0996 | 0.0000 | 0.0175 | 1.002 | 1.96 | 4735 |
| Nex710 Transgenic | 0.0352 | 0.0755 | 0.0000 | 0.0205 | 0.431 | 2.10 | 4740 |
| Mean | 0.0789 | 0.1676 | 0.0038 | 0.0165 | 0.814 | 1.65 | 4750 |
| Standard deviation | 0.0205 | 0.0745 | 0.0067 | 0.0056 | 0.1606 | 0.3031 | 48.8 |
| Minimum | 0.0352 | 0.05730 | 0.0000 | 0.0063 | 0.431 | 1.13 | 4621 |
| Maximum | 0.1240 | 0.3383 | 0.0217 | 0.0269 | 1.123 | 2.24 | 4821 |

Table 15 shows total amino acid content of meals from various varieties, including DN03-3746, which had the highest content of almost all the tested amino acids (including essential amino acids). Table 16 shows apparent ileal amino acid digestibility, for these lines, by the broiler chickens.

TABLE 15

Total amino acid content of meals from Nexera varieties (% dm basis, Year 2)

| Sample | CYS | ASP | MET | THR | SER | GLU |
|---|---|---|---|---|---|---|
| Nex 705 | 1.302 | 3.597 | 0.827 | 2.036 | 2.068 | 8.439 |
| Nex 715 | 1.350 | 3.295 | 0.784 | 2.914 | 2.060 | 8.891 |
| Nex 710 | 1.357 | 3.346 | 0.820 | 2.017 | 2.066 | 8.821 |
| Nex 720 | 1.407 | 3.246 | 0.824 | 1.939 | 2.025 | 9.019 |
| DN033746 | 1.473 | 3.586 | 0.870 | 2.131 | 2.194 | 9.390 |
| Check 1 | 1.215 | 3.119 | 0.778 | 1.872 | 1.894 | 8.011 |
| Check 2 | 1.293 | 3.284 | 0.805 | 1.960 | 1.963 | 8.513 |
| Nex 710 Null Transgenic | 1.378 | 3.937 | 0.894 | 2.227 | 2.244 | 9.900 |
| Nex 710 Transgenic | 1.368 | 3.839 | 0.855 | 2.125 | 2.092 | 9.587 |

| Sample | PRO | GLY | ALA | VAL | ISO | LEU |
|---|---|---|---|---|---|---|
| Nex 705 | 2.942 | 2.382 | 2.090 | 2.144 | 1.710 | 3.307 |
| Nex 715 | 2.844 | 2.330 | 2.039 | 2.155 | 1.706 | 3.266 |
| Nex 710 | 2.986 | 2.450 | 2.114 | 2.300 | 1.828 | 3.335 |
| Nex 720 | 3.045 | 2.389 | 2.078 | 2.218 | 1.766 | 3.263 |
| DN033746 | 2.746 | 2.526 | 2.280 | 2.470 | 1.963 | 3.557 |
| Check 1 | 2.463 | 2.253 | 1.970 | 2.175 | 1.733 | 3.093 |
| Check 2 | 2.837 | 2.414 | 2.027 | 2.315 | 1.813 | 3.249 |
| Nex 710 Null Transgenic | 3.074 | 2.730 | 2.357 | 2.611 | 2.090 | 3.772 |
| Nex 710 Transgenic | 3.077 | 2.636 | 2.279 | 2.616 | 2.063 | 3.643 |

| Sample | PHE | HIS | LYS | AMM | ARG |
|---|---|---|---|---|---|
| Nex 705 | 1.795 | 1.239 | 2.670 | 1.178 | 2.782 |
| Nex 715 | 1.765 | 1.289 | 2.683 | 1.187 | 2.895 |
| Nex 710 | 1.817 | 1.309 | 2.783 | 1.200 | 2.900 |
| Nex 720 | 1.765 | 1.312 | 2.742 | 1.198 | 2.867 |
| DN033746 | 1.947 | 1.346 | 2.993 | 1.270 | 3.028 |
| Check 1 | 1.656 | 1.238 | 2.670 | 1.114 | 2.663 |
| Check 2 | 1.771 | 1.288 | 2.719 | 1.191 | 2.887 |
| Nex 710 Null Transgenic | 2.049 | 1.527 | 3.019 | 1.354 | 3.270 |
| Nex 710 Transgenic | 1.969 | 1.459 | 2.956 | 1.308 | 3.205 |

TABLE 16

Apparent ileal amino acid digestibility (in broiler chickens) of Nexera canola varieties (Year 2)

| Sample | CYS | ASP | MET | THR | SER | GLU |
|---|---|---|---|---|---|---|
| Nex 705 | 0.727 | 0.788 | 0.885 | 0.683 | 0.721 | 0.873 |
| Nex 715 | 0.749 | 0.793 | 0.889 | 0.708 | 0.733 | 0.875 |
| Nex 710 | 0.783 | 0.820 | 0.913 | 0.748 | 0.758 | 0.902 |
| Nex 720 | 0.791 | 0.824 | 0.903 | 0.730 | 0.767 | 0.893 |
| DN033746 | 0.675 | 0.754 | 0.869 | 0.633 | 0.701 | 0.864 |
| Check 1 | 0.775 | 0.796 | 0.898 | 0.714 | 0.736 | 0.887 |
| Check 2 | 0.717 | 0.760 | 0.849 | 0.678 | 0.700 | 0.843 |
| Nex 710 Null Transgenic | 0.805 | 0.849 | 0.924 | 0.759 | 0.778 | 0.916 |
| Nex 710 Transgenic | 0.786 | 0.838 | 0.908 | 0.726 | 0.749 | 0.905 |
| SEM | 0.0038 | 0.0032 | 0.0025 | 0.0040 | 0.0036 | 0.0024 |
| P VALUE | 0.0001 | 0.0001 | 0.0001 | 0.0004 | 0.0025 | 0.0019 |

| Sample | PRO | GLY | ALA | VAL | ISO | LEU |
|---|---|---|---|---|---|---|
| Nex 705 | 0.719 | 0.771 | 0.811 | 0.737 | 0.762 | 0.798 |
| Nex 715 | 0.742 | 0.795 | 0.828 | 0.788 | 0.810 | 0.826 |
| Nex 710 | 0.785 | 0.821 | 0.850 | 0.811 | 0.830 | 0.842 |
| Nex 720 | 0.767 | 0.821 | 0.850 | 0.797 | 0.827 | 0.842 |
| DN033746 | 0.712 | 0.744 | 0.791 | 0.718 | 0.734 | 0.783 |
| Check 1 | 0.731 | 0.808 | 0.825 | 0.783 | 0.797 | 0.809 |
| Check 2 | 0.704 | 0.753 | 0.785 | 0.716 | 0.728 | 0.762 |
| Nex 710 Null Transgenic | 0.782 | 0.845 | 0.863 | 0.827 | 0.839 | 0.857 |
| Nex 710 Transgenic | 0.757 | 0.831 | 0.851 | 0.801 | 0.827 | 0.840 |
| SEM | 0.0038 | 0.0032 | 0.0030 | 0.0039 | 0.0038 | 0.0033 |
| P VALUE | 0.0003 | 0.0001 | 0.0014 | 0.0001 | 0.0001 | 0.0004 |

| Sample | PHE | HIS | LYS | AMM | ARG |
|---|---|---|---|---|---|
| Nex 705 | 0.831 | 0.859 | 0.820 | 0.743 | 0.883 |
| Nex 715 | 0.843 | 0.853 | 0.837 | 0.799 | 0.881 |
| Nex 710 | 0.866 | 0.892 | 0.869 | 0.809 | 0.912 |
| Nex 720 | 0.846 | 0.874 | 0.859 | 0.778 | 0.906 |
| DN033746 | 0.811 | 0.835 | 0.805 | 0.689 | 0.889 |
| Check 1 | 0.835 | 0.866 | 0.846 | 0.790 | 0.897 |
| Check 2 | 0.797 | 0.820 | 0.796 | 0.704 | 0.862 |
| Nex 710 Null Transgenic | 0.874 | 0.903 | 0.879 | 0.833 | 0.924 |
| Nex 710 Transgenic | 0.856 | 0.889 | 0.875 | 0.832 | 0.917 |
| SEM | 0.0030 | 0.0028 | 0.0029 | 0.0041 | 0.0022 |
| P VALUE | 0.0013 | 0.0001 | 0.0001 | 0.0001 | 0.0001 |

Again, these numbers and other numbers in Tables 12, 13, 14, 15, and 16 (and in any other Table) can be used to define end points of ranges of characteristics of seeds and lines of the subject invention.

EXAMPLE 8

Development of Still Further Lines—Year 4

The 6 BC1F5 lines that gave rise to the BC1F6 lines (DN033743, DN033744, DN033745, DN033746, DN033747, DN033748, DN033749) were crossed with the DAS black seeded NATREON line DN996738 (aka NQC02X01). F1 plants from each cross were taken through the microspore culture process and dihaploid progeny produced. The BC1F6 lines, DH progeny, and check varieties were evaluated in replicated nurseries at AAFC Saskatoon and Dow AgroSciences (DAS) Moonlake. Nursery plots were single 10 foot long rows, planted at a 2 foot row spacing, replicated up to 4 times across the two locations.

Agronomic assessments were made on Days to Flower (DTF), Days to Maturity (DTM), Lodging (LDG), and Late Season Vigor (LSV) at the DAS Moonlake site. Seed samples were collected from plots at both locations and analyzed for seed quality parameters by the respective organizations analytical chemistry labs with the exception of Whiteness index and fiber. Whiteness Index (WImini), a measurement of seed color, was produced from samples at both locations using the Hunter Analytical Instrument by AAFC. Seed fiber (Neutral Detergent Fiber=NDF, Acid Detergent Fiber=ADF, Acid Detergent Lignin=ADL) was determined on samples from the AAFC location using NIR and is expressed on a dry matter basis. Fatty acid composition was determined by gas chromatography using fatty acid methyl ester analysis. Individual fatty acids are reported as a percentage of the total profile and total saturates calculated by adding all of the saturated fatty acids. Oil content on a dry matter basis (DM), protein content (DM) of the seed, and total glucosinolate content were determined using NIR. Protein content expressed on an oil free meal basis (% Meal Protein DM) was calculated.

Colder than average growing conditions followed by an early fall frost impacted the trials at both sites, and can be noted in the lower than normally expected Oleic acid contents. These data were used to identify superior individuals expressing the desired fatty acid profile in combination with fiber reduction as well as acceptable maturity, and content of oil, protein, and glucosinolates. A summary of the mean quality data for BC1F6 progenies, DH progeny selected for advancement, and checks from the AAFC location are provided in Table 17. A summary of the mean agronomic and quality data for BC1F6 progenies, DH progeny selected for advancement, and checks from the DAS location are provided in Table 18.

TABLE 17

Mean quality data BC1F6 progenies, selected DH progenies and checks from a replicated nursery trial carried out at AAFC Saskatoon in Year 4

| SOURCE/ID | Code | % Oil DM | % Protein Seed DM | % Meal Protein DM | Total Gluc | ADFdm | ADLdm | NDFdm | WImini | C18:1 | C18:2 | C18:3 | C22:1 | % Saturates |
|---|---|---|---|---|---|---|---|---|---|---|---|---|---|---|
| DN03-3743 | 2672 | 43.0 | 27.4 | 48.1 | 26.1 | 9.5 | 1.9 | 18.3 | −13.1 | 63.2 | 22.9 | 2.8 | 0.1 | 7.0 |
| DN03-3744 | 2714 | 44.0 | 26.6 | 47.6 | 16.1 | 12.9 | 3.8 | 19.4 | −6.7 | | | | | |
| DN03-3745 | 2715 | 43.4 | 28.8 | 50.9 | 18.3 | 9.5 | 1.6 | 17.8 | −13.6 | | | | | |
| DN03-3746 | 2716 | 43.6 | 27.6 | 48.9 | 25.4 | 10.0 | 1.7 | 17.7 | −15.1 | 64.6 | 21.9 | 2.9 | 0.1 | 6.8 |
| DN03-3747 | 2717 | 41.1 | 27.9 | 47.4 | 23.3 | 10.1 | 1.9 | 18.4 | −13.1 | | | | | |
| DN03-3748 | 2718 | 44.0 | 26.6 | 47.6 | 18.0 | 9.4 | 1.7 | 18.2 | −13.1 | | | | | |
| DN03-3749 | 2719 | 42.4 | 28.6 | 49.6 | 18.4 | 10.0 | 1.8 | 18.6 | −12.5 | 65.2 | 20.6 | 3.2 | 0.2 | 6.9 |
| DN99-6738 | 2674 | 49.3 | 27.3 | 54.0 | 6.3 | 12.5 | 3.9 | 18.6 | −0.9 | 70.9 | 17.9 | 2.2 | 0.1 | 5.9 |
| Nex 705 | 2687 | 47.7 | 27.0 | 51.7 | 11.6 | 13.7 | 5.0 | 20.4 | −0.5 | 71.6 | 17.1 | 2.8 | 0.1 | 5.6 |
| YN01-429 | 2700 | 48.9 | 24.7 | 48.4 | 8.3 | 9.2 | 1.4 | 16.9 | −22.4 | | | | | |
| YN97-262 | 2673 | 44.4 | 26.1 | 46.9 | 5.8 | 10.2 | 2.1 | 18.5 | −13.8 | | | | | |
| DN04-1247 | 2205 | 46.1 | 26.8 | 49.7 | 10.3 | 10.0 | 1.9 | 17.5 | −11.5 | 67.3 | 20.8 | 2.2 | 0.1 | 6.4 |
| DN04-1261 | 2217 | 40.2 | 29.5 | 49.4 | 31.8 | 9.8 | 1.8 | 18.0 | −12.0 | 64.4 | 20.8 | 2.5 | 0.2 | 7.6 |
| DN04-1266 | 2221 | 45.6 | 28.0 | 51.6 | 14.9 | 9.9 | 1.9 | 17.1 | −14.3 | 67.0 | 20.8 | 2.5 | 0.1 | 6.2 |
| DN04-1273 | 2228 | 42.9 | 26.8 | 47.0 | 21.4 | 9.9 | 1.7 | 18.4 | −15.4 | 65.2 | 21.5 | 2.3 | 0.1 | 7.1 |
| DN04-1279 | 2233 | 44.5 | 28.1 | 50.6 | 16.7 | 9.9 | 1.9 | 17.8 | −12.4 | 67.4 | 19.6 | 2.5 | 0.1 | 7.0 |
| DN04-1317 | 2265 | 42.2 | 30.1 | 52.0 | 23.4 | 9.2 | 1.7 | 17.1 | −13.3 | | | | | |
| DN04-1326 | 2270 | 41.8 | 29.0 | 49.8 | 19.8 | 9.9 | 1.9 | 18.7 | −11.6 | 64.9 | 21.2 | 2.5 | 0.1 | 7.4 |
| DN04-1358 | 2297 | 44.9 | 30.0 | 54.4 | 6.6 | 9.1 | 1.7 | 17.0 | −15.4 | 66.3 | 20.9 | 2.8 | 0.1 | 6.5 |
| DN04-1371 | 2308 | 46.0 | 28.0 | 51.8 | 12.3 | 10.0 | 1.9 | 17.5 | −12.5 | 65.8 | 22.0 | 2.3 | 0.1 | 6.4 |
| DN04-1415 | 2346 | 48.4 | 26.8 | 51.9 | 10.6 | 9.5 | 1.6 | 17.5 | −16.0 | 66.3 | 20.4 | 3.0 | 0.1 | 6.7 |
| DN04-1495 | 2408 | 47.9 | 27.1 | 52.0 | 17.0 | 10.1 | 2.1 | 17.3 | −13.2 | | | | | |
| DN04-1506 | 2419 | 43.0 | 28.9 | 50.8 | 24.3 | 10.1 | 2.0 | 18.4 | −9.2 | | | | | |
| DN04-1510 | 2423 | 44.9 | 30.2 | 54.7 | 15.8 | 9.6 | 2.5 | 17.5 | −11.5 | | | | | |
| DN04-1516 | 2429 | 43.4 | 28.5 | 50.3 | 15.1 | 9.0 | 1.8 | 18.3 | −12.7 | | | | | |
| DN04-1524 | 2434 | 41.4 | 31.4 | 53.7 | 15.6 | 8.9 | 1.8 | 17.6 | −12.9 | | | | | |
| DN04-1537 | 2445 | 44.2 | 28.0 | 50.2 | 16.1 | 11.1 | 2.9 | 18.3 | −4.8 | | | | | |
| DN04-1593 | 2490 | 50.3 | 25.6 | 51.5 | 6.8 | 11.4 | 2.6 | 18.0 | −7.5 | | | | | |
| DN04-1709 | 2573 | 46.2 | 28.4 | 52.7 | 16.4 | 9.6 | 1.8 | 16.4 | −14.8 | 68.8 | 19.0 | 2.6 | 0.1 | 6.3 |
| DN04-1718 | 2580 | 42.3 | 28.7 | 49.7 | 17.4 | 10.3 | 2.0 | 18.2 | −11.8 | 65.4 | 21.7 | 2.4 | 0.1 | 6.8 |
| DN04-1768 | 2616 | 46.2 | 25.8 | 47.9 | 11.7 | 11.0 | 2.0 | 17.1 | −11.4 | 67.5 | 19.9 | 2.1 | 0.1 | 7.1 |

TABLE 18

Mean agronomic and quality data for BC1F6 progenies, selected DH progenies and checks from a replicated nursery trial carried out at AAFC Saskatoon in Year 4

| Name | Source Pop | DTF | DTM | LDG | LSV 1 | LSV 2 | C18:1 | C18:2 | C18:3 | % Sats | % Oil DM | % Protein DM | % Meal Protein DM | WImini | Tot Gluc |
|---|---|---|---|---|---|---|---|---|---|---|---|---|---|---|---|
| Nex 705 | Polo/SVO95-09 | 57 | 114 | 3.0 | 3.1 | 2.7 | 73.0 | 16.0 | 2.6 | 5.7 | 51.4 | 21.0 | 43.2 | 0.0 | 14.9 |
| YN01429 | . | 58 | 114 | 3.0 | 3.1 | 2.7 | 60.1 | 20.4 | 11.0 | 6.0 | 54.3 | 22.0 | 48.3 | −26.5 | 16.2 |
| YN97262 | . | 53 | 112 | 3.0 | 3.0 | 3.0 | 60.9 | 20.9 | 8.9 | 7.0 | 50.9 | 23.4 | 47.6 | −20.7 | 14.3 |
| DN033748 | DN023434 | 51 | 114 | 3.0 | 4.0 | 4.0 | 68.0 | 21.6 | 2.1 | 5.6 | 48.9 | 23.1 | 45.3 | −20.6 | 13.0 |
| DN033746 | DN023431 | 58 | 112 | 3.0 | 3.0 | 3.0 | 68.4 | 20.5 | 2.1 | 6.5 | 51.2 | 22.8 | 46.8 | −24.0 | 12.0 |
| DN041247 | DN023429/DN996738 | 57 | 115 | 3.5 | 3.0 | 2.5 | 68.7 | 19.9 | 2.2 | 6.4 | 50.2 | 22.9 | 46.0 | −15.2 | 12.7 |
| DN041261 | DN023429/DN996738 | 57 | 113 | 3.5 | 3.5 | 3.5 | 69.9 | 18.9 | 2.3 | 6.2 | 47.9 | 23.6 | 45.3 | −15.0 | 17.6 |

TABLE 18-continued

Mean agronomic and quality data for BC1F6 progenies, selected DH progenies and checks from a replicated nursery trial carried out at AAFC Saskatoon in Year 4

| Name | Source Pop | DTF | DTM | LDG | LSV 1 | LSV 2 | C18:1 | C18:2 | C18:3 | % Sats | % Oil DM | % Protein DM | % Meal Protein DM | WImini | Tot Gluc |
|---|---|---|---|---|---|---|---|---|---|---|---|---|---|---|---|
| DN041266 | DN023429/DN996738 | 55 | 114 | 3.5 | 4.0 | 3.5 | 70.0 | 19.3 | 2.3 | 5.6 | 48.6 | 23.7 | 46.1 | −16.4 | 15.0 |
| DN041273 | DN023429/DN996738 | 58 | 115 | 3.0 | 4.0 | 3.5 | 68.5 | 20.2 | 2.2 | 6.4 | 48.4 | 23.6 | 45.8 | −16.3 | 11.5 |
| DN041279 | DN023429/DN996738 | 57 | 112 | 3.5 | 4.0 | 3.5 | 69.9 | 17.9 | 2.5 | 6.9 | 49.3 | 22.8 | 45.0 | −14.6 | 14.7 |
| DN041317 | DN023429/DN996738 | 58 | 115 | 3.5 | 4.0 | 3.5 | 68.2 | 20.1 | 2.4 | 6.4 | 49.5 | 23.1 | 45.8 | −16.3 | 17.2 |
| DN041326 | DN023429/DN996738 | 58 | 114 | 3.0 | 4.0 | 3.0 | 69.1 | 19.4 | 2.3 | 6.6 | 52.0 | 22.2 | 46.2 | −18.8 | 16.6 |
| DN041358 | DN023430/DN996738 | 60 | 114 | 3.0 | 3.0 | 2.5 | 70.3 | 18.1 | 2.4 | 6.4 | 49.0 | 22.2 | 43.6 | −20.1 | 13.7 |
| DN041371 | DN023430/DN996738 | 60 | 115 | 3.0 | 4.0 | 3.5 | 68.7 | 19.9 | 2.5 | 6.1 | 49.2 | 22.7 | 44.8 | −13.9 | 15.0 |
| DN041415 | DN023430/DN996738 | 60 | 111 | 3.0 | 4.0 | 3.5 | 69.2 | 18.5 | 3.1 | 6.4 | 50.6 | 22.5 | 45.5 | −19.9 | 11.7 |
| DN041495 | DN023431/DN996738 | 60 | 114 | 2.5 | 3.5 | 3.5 | 69.9 | 19.4 | 2.3 | 5.8 | 50.4 | 22.2 | 44.8 | −15.8 | 16.0 |
| DN041506 | DN023431/DN996738 | 67 | 114 | 2.5 | 4.0 | 4.0 | 70.0 | 19.1 | 2.5 | 5.9 | 50.8 | 22.9 | 46.5 | −13.6 | 13.5 |
| DN041510 | DN023431/DN996738 | 59 | 114 | 3.0 | 4.0 | 3.0 | 72.1 | 17.3 | 2.0 | 6.0 | 52.5 | 21.1 | 44.5 | −13.8 | 13.7 |
| DN041516 | DN023431/DN996738 | 58 | 114 | 3.0 | 4.5 | 4.0 | 68.4 | 20.3 | 2.2 | 6.0 | 50.3 | 22.1 | 44.4 | −17.2 | 13.8 |
| DN041524 | DN023431/DN996738 | 67 | 115 | 3.0 | 4.0 | 3.5 | 69.0 | 19.8 | 2.5 | 6.0 | 48.6 | 22.5 | 43.8 | −19.4 | 15.5 |
| DN041537 | DN023431/DN996738 | 60 | 115 | 3.0 | 3.5 | 2.5 | 70.4 | 19.1 | 2.1 | 5.5 | 53.8 | 21.8 | 47.3 | −8.2 | 15.3 |
| DN041593 | DN023433/DN996738 | 61 | 114 | 3.0 | 4.0 | 4.0 | 73.5 | 15.5 | 2.3 | 6.2 | 53.4 | 21.6 | 46.4 | −10.6 | 13.8 |
| DN041667 | DN023434/DN996738 | 56 | 116 | 3.0 | 5.0 | 3.0 | 72.3 | 16.9 | 1.8 | 6.2 | 53.3 | 22.4 | 48.0 | −14.0 | 12.2 |
| DN041709 | DN023434/DN996738 | 57 | 116 | 3.0 | 5.0 | 4.0 | 70.7 | 18.0 | 2.5 | 6.1 | 46.4 | 24.1 | 45.1 | −14.3 | 17.4 |
| DN041718 | DN023434/DN996738 | 57 | 116 | 3.0 | 3.0 | 3.0 | 69.8 | 19.3 | 2.1 | 6.3 | 52.3 | 22.3 | 46.7 | −15.7 | 14.8 |
| DN041768 | DN023435/DN996738 | 59 | 114 | 3.0 | 3.0 | 2.5 | 69.0 | 19.5 | 2.1 | 6.4 | 51.0 | 22.8 | 46.6 | −10.9 | 14.5 |

EXAMPLE 9

Yield Trials—Year 5

The DH progeny summarized in Tables 17 and 18 were selected for advancement into replicated yield trials conducted in Year 5. Twenty-one DH progeny along with 2 BC1F6 lines, and yellow seeded as well as black seeded checks were compared under small plot conditions using a 4 replicate Randomized Complete Block design. Four locations (DAS Rosthern, DAS Saskatoon, DAS Moonlake, AAFC Saskatoon) were planted in Year 5.

Heavy rains and flooding resulted in the complete loss of the Moonlake trial, and two replicates of the AAFC Saskatoon location and unacceptable plant stand at the Rosthern location resulted in data from that site being discarded. Below average temperatures were experienced in Year 5.

Agronomic assessments were made on Days to Flower (DTF), Days to Maturity (DTM), Height (HGT), and Lodging (LDG). Plots were harvested using small plot harvest equipment. Yield was determined by measuring the quantity of seed harvested from each plot and expressing it on a kilograms per hectare basis. Seed quality parameters (Oil DM, Protein DM, Total Glucosinolates, % NDFdm, % ADFdm, % ADLdm, Chlorophyll) were measured using NIR by the respective organizations analytical chemistry labs. Protein content expressed on an oil free meal basis (% Meal Protein DM) was calculated. Whiteness Index (WI) was measured by AAFC on samples from the AAFC Saskatoon location using the Hunter Analytical Instrument. Fatty acid composition was determined by gas chromatography, using fatty acid methyl ester analysis. Individual fatty acids are reported as a percentage of the total profile and total saturates calculated by adding all of the saturated fatty acids.

Data confirmed that lines with the combination of a desired fatty acid profile similar to the Nexera check varieties and reduced level of fiber similar to the yellow seeded canola checks were advanced from the nurseries in Year 4. The additional agronomic data on maturity, height, and lodging as well as the seed yield reveals that several of the advanced DH lines are competitive with industry standards and Nexera check varieties. See Tables 19 and 20.

Yields achieved, as reported in Tables 19 and 20, are especially noteworthy.

TABLE 19

Mean agronomic and quality data for BC1F6 progenies, selected DH progenies and checks from a replicated yield trial carried out at AAFC Saskatoon in Year 5

| EXPT | NAME | DTF | DTM | Seed Yield kg/ha | C18:1 | C18:2 | C18:3 | C22:1 | % Saturates | % Oil DM | % Protein Seed DM | % Meal Protein DM | Tot Gluc | % ADF dm | % ADL dm | % NDF dm | WI |
|---|---|---|---|---|---|---|---|---|---|---|---|---|---|---|---|---|---|
| 05RYT28 | Q2 | 43.5 | 96.0 | 2706 | 62.25 | 19.68 | 9.25 | 0.04 | 6.15 | 48.8 | 25.5 | 49.7 | 20.0 | 19.6 | 8.5 | 22.9 | 2.5 |
| 05RYT28 | 46A65 | 44.5 | 96.0 | 2064 | 60.03 | 20.04 | 10.54 | 0.09 | 6.72 | 47.5 | 24.9 | 47.4 | 7.8 | 16.4 | 5.9 | 21.7 | 2.8 |
| 05RYT28 | Nex 705 | 44.0 | 101.5 | 2798 | 72.56 | 16.48 | 2.57 | 0.04 | 5.80 | 50.7 | 25.7 | 52.1 | 11.5 | 15.4 | 5.9 | 20.6 | 1.8 |
| 05RYT28 | Nex 715 | 44.5 | 98.5 | 2482 | 74.18 | 14.34 | 2.81 | 0.04 | 6.07 | 46.7 | 26.6 | 49.8 | 23.8 | 18.8 | 8.6 | 22.9 | 1.3 |
| 05RYT28 | Nex 822 CL | 46.0 | 97.0 | 2492 | 71.19 | 17.32 | 2.32 | 0.03 | 5.98 | 47.2 | 28.4 | 53.8 | 11.0 | 13.9 | 4.5 | 18.9 | 1.7 |
| 05RYT28 | YN97-262 | 44.5 | 96.5 | 3121 | 59.84 | 21.56 | 9.22 | 0.04 | 6.81 | 48.3 | 24.9 | 48.2 | 16.0 | 13.0 | 3.8 | 18.7 | −17.0 |
| 05RYT28 | YN01-429 | 46.0 | 101.0 | 2807 | 60.12 | 21.82 | 8.86 | 0.03 | 6.65 | 49.8 | 23.1 | 46.0 | 20.3 | 10.8 | 2.0 | 16.9 | −27.5 |
| 05RYT28 | DN03-3746 | 47.0 | 101.5 | 2319 | 65.96 | 20.94 | 3.41 | 0.06 | 6.82 | 48.3 | 24.9 | 48.2 | 22.8 | 10.2 | 1.4 | 17.0 | −24.5 |
| 05RYT28 | DN03-3748 | 46.0 | 99.0 | 2188 | 64.94 | 20.94 | 4.73 | 0.03 | 6.58 | 48.9 | 24.6 | 48.1 | 21.6 | 11.0 | 2.1 | 17.6 | −21.4 |
| 05RYT28 | DN04-1667 | 44.5 | 100.0 | 1522 | 70.74 | 17.84 | 2.07 | 0.03 | 6.62 | 51.2 | 24.6 | 50.4 | 13.6 | 10.6 | 2.2 | 16.7 | −17.1 |
| 05RYT28 | DN04-1709 | 44.0 | 98.5 | 2267 | 70.97 | 17.62 | 2.49 | 0.03 | 6.21 | 50.6 | 25.7 | 52.1 | 15.7 | 11.2 | 2.5 | 16.6 | −16.5 |
| 05RYT28 | DN04-1358 | 48.0 | 102.5 | 2291 | 70.77 | 17.49 | 2.20 | 0.04 | 6.78 | 49.6 | 26.2 | 52.0 | 17.8 | 10.4 | 1.9 | 15.9 | −19.7 |
| 05RYT28 | DN04-1506 | 48.5 | 97.5 | 2805 | 69.36 | 18.76 | 2.26 | 0.03 | 6.83 | 49.7 | 25.4 | 50.5 | 10.6 | 13.1 | 3.5 | 18.8 | −4.5 |
| 05RYT28 | DN04-1266 | 44.5 | 99.5 | 2319 | 68.69 | 19.59 | 2.42 | 0.06 | 6.32 | 48.5 | 25.6 | 49.7 | 28.3 | 11.7 | 2.6 | 17.8 | −17.1 |
| 05RYT28 | DN04-1279 | 46.0 | 101.0 | 2396 | 70.09 | 17.86 | 2.17 | 0.09 | 7.02 | 50.1 | 25.3 | 50.7 | 14.4 | 11.5 | 2.5 | 17.3 | −15.0 |
| 05RYT28 | DN04-1495 | 47.5 | 100.5 | 2414 | 69.46 | 19.00 | 2.40 | 0.04 | 6.40 | 48.8 | 25.7 | 50.3 | 22.1 | 11.1 | 2.3 | 17.3 | −16.1 |
| 05RYT28 | DN04-1261 | 46.5 | 100.0 | 1938 | 68.71 | 19.44 | 2.49 | 0.03 | 6.56 | 47.9 | 26.1 | 50.0 | 18.1 | 11.6 | 2.6 | 17.4 | −13.8 |
| 05RYT28 | DN04-1718 | 44.5 | 100.5 | 2028 | 68.43 | 19.76 | 2.29 | 0.03 | 6.66 | 49.1 | 25.6 | 50.3 | 18.5 | 11.3 | 2.3 | 17.3 | −16.5 |
| 05RYT28 | DN04-1415 | 48.5 | 102.0 | 2185 | 68.55 | 18.86 | 2.79 | 0.04 | 7.01 | 49.3 | 24.0 | 47.3 | 24.8 | 11.1 | 1.8 | 17.6 | −20.6 |
| 05RYT28 | DN04-1326 | 46.5 | 100.5 | 2207 | 70.23 | 18.23 | 2.15 | 0.07 | 6.66 | 49.9 | 25.7 | 51.4 | 12.9 | 12.4 | 3.5 | 18.4 | −7.9 |
| 05RYT28 | DN04-1768 | 46.0 | 99.0 | 2045 | 68.98 | 19.14 | 2.15 | 0.04 | 7.03 | 50.1 | 24.1 | 48.3 | 19.0 | 12.3 | 2.6 | 18.5 | −13.3 |
| 05RYT28 | DN04-1247 | 45.5 | 99.0 | 2305 | 68.56 | 19.63 | 2.38 | 0.03 | 6.65 | 48.8 | 25.7 | 50.3 | 23.8 | 11.4 | 2.6 | 17.2 | −15.7 |
| 05RYT28 | DN04-1516 | 47.0 | 101.0 | 2012 | 68.61 | 19.74 | 2.17 | 0.03 | 6.58 | 48.4 | 25.0 | 48.5 | 20.0 | 10.3 | 1.6 | 17.2 | −19.7 |
| 05RYT28 | DN04-1524 | 49.0 | 102.0 | 1956 | 70.05 | 18.30 | 2.24 | 0.02 | 6.70 | 48.1 | 26.2 | 50.5 | 16.1 | 11.3 | 2.5 | 17.2 | −13.5 |
| 05RYT28 | DN04-1317 | 46.5 | 100.0 | 1901 | 67.29 | 20.73 | 2.27 | 0.05 | 6.80 | 49.6 | 26.1 | 51.7 | 27.4 | 11.0 | 2.0 | 16.0 | −23.5 |
| 05RYT28 | DN04-1371 | 48.0 | 102.0 | 2026 | 68.96 | 19.43 | 2.26 | 0.08 | 6.52 | 49.9 | 24.6 | 49.2 | 17.1 | 11.5 | 2.2 | 17.5 | −14.5 |
| 05RYT28 | DN04-1273 | 46.5 | 100.5 | 2415 | 68.01 | 20.15 | 2.20 | 0.05 | 6.78 | 49.0 | 23.7 | 46.4 | 21.5 | 10.8 | 1.9 | 17.8 | −21.6 |
| 05RYT28 | DN04-1593 | 49.0 | 101.0 | 2939 | 71.90 | 17.12 | 2.13 | 0.02 | 6.31 | 50.9 | 25.0 | 50.9 | 10.0 | 13.0 | 3.3 | 18.4 | −7.1 |
| 05RYT28 | DN04-1510 | 46.0 | 99.0 | 2322 | 70.19 | 18.51 | 2.05 | 0.04 | 6.57 | 49.6 | 26.6 | 52.8 | 17.5 | 11.3 | 2.7 | 17.4 | −14.5 |
| 05RYT28 | DN04-1537 | 47.5 | 99.0 | 3032 | 69.95 | 18.88 | 2.17 | 0.03 | 6.32 | 50.6 | 24.7 | 50.0 | 7.9 | 13.8 | 3.8 | 19.5 | −4.5 |

TABLE 20

Mean agronomic and quality data for BC1F6 progenies, selected DH progenies and checks from a replicated yield trial carried out at DAS Saskatoon in Year 5

| Field Name | Name | DTF | DTM | HGT | LDG | Yield (Kg/Ha) | C18:1 | C18:2 | C18:3 | C22:1 |
|---|---|---|---|---|---|---|---|---|---|---|
| MSSAS:RYT | Q2 | 53.0 | 102.0 | 97 | 2.0 | 2209 | 60.6 | 19.0 | 10.4 | 0.2 |
| MSSAS:RYT | 46A65 | 51.3 | 100.0 | 100 | 2.0 | 2280 | 61.9 | 19.4 | 9.4 | 0.0 |
| MSSAS:RYT | Nex 705 | 52.0 | 110.0 | 98 | 2.0 | 2151 | 72.2 | 16.2 | 2.8 | 0.0 |
| MSSAS:RYT | Nex 715 | 52.7 | 99.3 | 93 | 2.7 | 2015 | 72.5 | 15.4 | 2.9 | 0.1 |
| MSSAS:RYT | Nex 822 CL | 54.0 | 106.3 | 93 | 2.3 | 2047 | 70.9 | 17.5 | 2.4 | 0.0 |
| MSSAS:RYT | YN97262 | 53.3 | 107.3 | 103 | 2.0 | 2622 | 59.9 | 21.5 | 8.9 | 0.0 |
| MSSAS:RYT | YN01429 | 53.0 | 108.7 | 103 | 2.0 | 2263 | 60.1 | 21.3 | 8.8 | 0.0 |
| MSSAS:RYT | DN033746 | 56.0 | 112.3 | 97 | 2.0 | 1821 | 66.7 | 20.7 | 2.4 | 0.0 |
| MSSAS:RYT | DN033748 | 51.8 | 110.5 | 98 | 2.0 | 1734 | 66.9 | 20.4 | 3.0 | 0.0 |
| MSSAS:RYT | DN041247 | 54.3 | 108.3 | 115 | 2.0 | 1756 | 68.7 | 19.0 | 2.2 | 0.2 |
| MSSAS:RYT | DN041261 | 55.0 | 111.7 | 97 | 2.0 | 1480 | 67.7 | 20.3 | 2.4 | 0.1 |
| MSSAS:RYT | DN041266 | 53.3 | 109.3 | 100 | 2.7 | 1483 | 69.0 | 19.1 | 2.3 | 0.0 |
| MSSAS:RYT | DN041273 | 54.7 | 110.7 | 97 | 2.3 | 1885 | 68.5 | 19.6 | 2.2 | 0.0 |
| MSSAS:RYT | DN041279 | 55.0 | 111.0 | 97 | 2.0 | 2273 | 69.8 | 17.8 | 2.4 | 0.0 |
| MSSAS:RYT | DN041317 | 55.3 | 110.5 | 93 | 2.5 | 1680 | 67.1 | 20.6 | 2.4 | 0.0 |
| MSSAS:RYT | DN041326 | 55.0 | 111.3 | 100 | 2.0 | 1720 | 67.2 | 20.1 | 2.6 | 0.0 |
| MSSAS:RYT | DN041358 | 55.7 | 112.7 | 110 | 2.0 | 1810 | 69.9 | 17.7 | 2.4 | 0.0 |
| MSSAS:RYT | DN041371 | 55.3 | 112.3 | 103 | 2.0 | 1839 | 69.1 | 18.6 | 2.5 | 0.0 |
| MSSAS:RYT | DN041415 | 56.3 | 113.3 | 97 | 2.0 | 1896 | 68.1 | 18.9 | 2.6 | 0.0 |
| MSSAS:RYT | DN041495 | 55.3 | 112.0 | 100 | 2.0 | 2331 | 69.4 | 19.1 | 2.3 | 0.0 |
| MSSAS:RYT | DN041506 | 55.3 | 107.7 | 110 | 1.7 | 2679 | 69.2 | 18.5 | 2.2 | 0.0 |
| MSSAS:RYT | DN041510 | 55.0 | 109.0 | 110 | 2.0 | 2421 | 70.8 | 17.7 | 2.1 | 0.0 |
| MSSAS:RYT | DN041516 | 55.7 | 112.0 | 98 | 2.0 | 2043 | 68.7 | 19.5 | 2.2 | 0.0 |
| MSSAS:RYT | DN041524 | 56.0 | 112.3 | 97 | 2.0 | 1350 | 68.8 | 18.9 | 2.3 | 0.0 |
| MSSAS:RYT | DN041537 | 55.7 | 110.7 | 103 | 2.0 | 2575 | 70.0 | 18.5 | 2.3 | 0.0 |
| MSSAS:RYT | DN041593 | 54.7 | 111.7 | 105 | 1.3 | 2737 | 71.6 | 16.7 | 2.4 | 0.0 |

TABLE 20-continued

Mean agronomic and quality data for BC1F6 progenies, selected DH progenies and checks from a replicated yield trial carried out at DAS Saskatoon in Year 5

| MSSAS:RYT | DN041667 | 53.3 | 108.0 | 97 | 2.0 | 2259 | 69.4 | 18.1 | 2.2 | 0.0 |
|---|---|---|---|---|---|---|---|---|---|---|
| MSSAS:RYT | DN041709 | 52.7 | 108.3 | 90 | 2.0 | 2133 | 71.4 | 17.2 | 2.2 | 0.0 |
| MSSAS:RYT | DN041718 | 52.7 | 111.0 | 93 | 2.0 | 1670 | 68.9 | 19.0 | 2.4 | 0.1 |
| MSSAS:RYT | DN041768 | 55.0 | 110.0 | 90 | 2.0 | 1799 | 70.0 | 18.1 | 2.0 | 0.0 |

| Field Name | Name | % Sats | % Oil DM | % Protein Seed DM | % Meal Protein DM | Tot Gluc | % NDF dm | % ADF dm | Chlorophyll PPM |
|---|---|---|---|---|---|---|---|---|---|
| MSSAS:RYT | Q2 | 6.9 | 47.6 | 24.1 | 46.0 | 13.4 | 24.9 | 15.0 | 16.2 |
| MSSAS:RYT | 46A65 | 6.6 | 48.4 | 22.5 | 43.7 | 18.9 | 26.7 | 16.9 | 9.6 |
| MSSAS:RYT | Nex 705 | 6.2 | 51.0 | 22.1 | 45.2 | 11.1 | 25.5 | 14.1 | 13.3 |
| MSSAS:RYT | Nex 715 | 6.5 | 45.6 | 23.9 | 44.0 | 11.0 | 26.9 | 17.9 | 11.7 |
| MSSAS:RYT | Nex 822 CL | 6.2 | 46.3 | 24.1 | 44.8 | 13.4 | 22.0 | 11.8 | 10.5 |
| MSSAS:RYT | YN97262 | 7.0 | 50.1 | 25.2 | 50.5 | 13.5 | 18.7 | 9.4 | 4.6 |
| MSSAS:RYT | YN01429 | 6.9 | 49.6 | 26.0 | 51.5 | 11.2 | 20.0 | 10.3 | 9.9 |
| MSSAS:RYT | DN033746 | 7.1 | 48.4 | 25.8 | 50.0 | 7.7 | 21.8 | 10.9 | 25.1 |
| MSSAS:RYT | DN033748 | 6.5 | 48.2 | 25.5 | 49.2 | 11.0 | 20.1 | 10.4 | 14.6 |
| MSSAS:RYT | DN041247 | 7.1 | 49.4 | 24.9 | 49.2 | 9.4 | 21.3 | 11.3 | 13.0 |
| MSSAS:RYT | DN041261 | 6.4 | 48.0 | 25.0 | 48.1 | 12.5 | 21.1 | 10.9 | 13.1 |
| MSSAS:RYT | DN041266 | 6.6 | 48.4 | 25.0 | 48.5 | 9.9 | 22.7 | 11.3 | 21.1 |
| MSSAS:RYT | DN041273 | 6.8 | 49.2 | 25.5 | 50.1 | 8.2 | 22.1 | 10.9 | 23.7 |
| MSSAS:RYT | DN041279 | 7.2 | 50.8 | 24.8 | 50.3 | 6.3 | 23.1 | 12.2 | 17.9 |
| MSSAS:RYT | DN041317 | 7.0 | 48.9 | 25.3 | 49.6 | 10.3 | 21.6 | 10.6 | 21.0 |
| MSSAS:RYT | DN041326 | 7.2 | 48.0 | 25.3 | 48.6 | 10.9 | 21.0 | 11.0 | 19.8 |
| MSSAS:RYT | DN041358 | 7.1 | 47.3 | 25.4 | 48.3 | 8.9 | 19.4 | 10.2 | 16.7 |
| MSSAS:RYT | DN041371 | 7.0 | 49.3 | 25.0 | 49.3 | 10.8 | 22.7 | 12.5 | 18.5 |
| MSSAS:RYT | DN041415 | 7.3 | 47.2 | 26.1 | 49.4 | 6.9 | 21.5 | 11.1 | 37.8 |
| MSSAS:RYT | DN041495 | 6.4 | 50.2 | 24.7 | 49.7 | 12.8 | 22.4 | 11.1 | 20.6 |
| MSSAS:RYT | DN041506 | 7.0 | 48.1 | 25.0 | 48.1 | 9.1 | 21.4 | 12.7 | 32.0 |
| MSSAS:RYT | DN041510 | 6.7 | 50.7 | 23.9 | 48.5 | 9.9 | 20.6 | 10.7 | 9.5 |
| MSSAS:RYT | DN041516 | 6.8 | 49.5 | 25.0 | 49.5 | 8.8 | 20.1 | 10.4 | 22.9 |
| MSSAS:RYT | DN041524 | 7.1 | 45.4 | 25.7 | 47.0 | 7.7 | 20.7 | 11.2 | 42.2 |
| MSSAS:RYT | DN041537 | 6.6 | 51.8 | 23.9 | 49.6 | 12.2 | 23.1 | 12.2 | 28.5 |
| MSSAS:RYT | DN041593 | 6.6 | 51.2 | 24.1 | 49.4 | 8.7 | 22.5 | 11.9 | 16.4 |
| MSSAS:RYT | DN041667 | 7.2 | 51.0 | 24.7 | 50.3 | 8.4 | 19.0 | 10.8 | 24.6 |
| MSSAS:RYT | DN041709 | 6.4 | 49.3 | 25.0 | 49.3 | 13.8 | 18.6 | 9.8 | 21.0 |
| MSSAS:RYT | DN041718 | 6.8 | 50.2 | 24.4 | 49.1 | 12.8 | 20.5 | 10.4 | 24.2 |
| MSSAS:RYT | DN041768 | 7.2 | 50.6 | 24.6 | 49.8 | 9.2 | 22.3 | 12.0 | 27.0 |

EXAMPLE 10

Further Feeding Study

Seven of the highest yielding DH lines as well as yellow and black seeded checks, observed in the Year 5 replicated yield trials, were selected for use in Poultry feeding trials to assess amino acid digestibility and energy content of meal from lower fiber yellow seeded lines in comparison to yellow and black seeded canola lines. Fifteen hundred grams of seed of each line selected for feeding, harvested from the first replicate of the Year 5 DAS Saskatoon yield trial was cold pressed, using a continuous screw press (Komet, type CA59; IBG Monforts Ockotec Gmbttt&Co Germany), and hexane extracted. Hexane extraction was achieved by immersing the remaining solids in hexane in sealed vessel at room temperature for 16 hours. After contact period the bulk of the hexane was decanted from the sample and the sample was placed in a large funnel lined with a paper tower to allow remaining solvent to drain. Samples were allowed to evaporate for 1 day in a shallow pan in a fume hood so that hexane was removed. Residual oil content was determined on 3 gram subsamples using a GoldfischExtractor with hexane as a solvent (model 22166B, Labconco Corp.; Kansas city, Mo., 64132, U.S.A.), comparing the weight of sample before solvent extraction and after. Residual moisture content was determine by weighing 1 gram subsamples of meal before and after drying with forced air at 130 degrees celcius for 2 hours.

Ground canola meal samples were tested for true metabolizable energy content ($TME_n$) and amino acid (AA) digestibility in poultry. The techniques being employed to measure $TME_n$ and AA digestibility are based on the regression analysis technique. This method of bioassay was first described by Sibbald (1976) for use in the measurement of true metabolizable energy in feedstuffs, and further adapted to account for energy retained in the bird as nitrogen (Sibbald, 1979). The method used for this study to measure both $TME_n$ and amino acid digestibility is described by Parsons et al. (1997). Following a 24-hr period without feed, birds were given 30-gram portions of the test diet via crop intubation, while additional birds were deprived of feed during the entire experimental period to measure endogenous excretion of dry matter, energy, nitrogen and amino acids. A plastic tray was placed under each bird's cage, and excreta was collected quantitatively for 48 hours after intubation. The excreta samples were then lyophilized, weighed, and ground to pass through a 60-mesh screen. Gross energy, nitrogen, and amino acid concentrations were then determined on at least two replicates of each individual sample of excreta. True digestibilities of amino acids are calculated according to the method described by Sibbald (1979), and $TME_n$ by the method of Parsons et al. (1982). $TME_n$ was corrected to 0% oil using a conversion that 1% oil contributes 80 Kcal of energy but displaces 25 Kcal of protein energy, therefore every 1% residual oil adds 55 Kcal of non-protein energy.

Results are provided in Tables 21 and 22.

TABLE 21

Amino Acid Digestibility (Percent) for meal prepared from DH lines, yellow seeded canola lines, and black seeded canola lines

| Line | Asp | Thr | Ser | Glu | Pro | Ala | Cys | Val | Met | Iso | Leu | Tyr | Phe | His | Lys | Arg | Try |
|---|---|---|---|---|---|---|---|---|---|---|---|---|---|---|---|---|---|
| DN041279 | 90.60 | 85.26 | 87.10 | 94.89 | 87.55 | 90.31 | 86.67 | 87.31 | 94.12 | 90.08 | 92.00 | 89.29 | 92.55 | 91.71 | 92.13 | 93.40 | 97.41 |
| DN041495 | 90.64 | 86.56 | 88.24 | 94.86 | 86.92 | 90.27 | 86.57 | 86.61 | 94.86 | 89.53 | 92.82 | 90.06 | 93.58 | 92.97 | 92.08 | 95.18 | 97.19 |
| DN041506 | 90.11 | 87.19 | 89.06 | 94.77 | 87.73 | 90.29 | 89.85 | 87.71 | 94.17 | 89.42 | 92.23 | 90.03 | 92.45 | 92.55 | 93.39 | 93.55 | 97.14 |
| DN041510 | 90.60 | 86.51 | 89.29 | 94.49 | 87.32 | 89.51 | 86.08 | 87.03 | 93.84 | 89.08 | 92.29 | 89.54 | 92.75 | 91.63 | 92.02 | 91.87 | 97.18 |
| DN041537 | 87.36 | 83.46 | 85.37 | 92.68 | 85.88 | 86.14 | 83.58 | 83.66 | 92.02 | 85.10 | 89.12 | 87.01 | 90.25 | 90.53 | 91.76 | 93.13 | 96.69 |
| DN041593 | 90.22 | 87.48 | 90.03 | 94.57 | 89.01 | 90.03 | 88.03 | 87.73 | 93.95 | 88.79 | 92.14 | 90.12 | 92.78 | 91.03 | 93.32 | 94.36 | 96.83 |
| DN041667 | 89.69 | 87.20 | 90.08 | 94.35 | 87.82 | 88.22 | 88.25 | 84.61 | 93.56 | 86.42 | 91.02 | 89.53 | 92.20 | 91.30 | 92.97 | 94.50 | 87.81 |
| YN97262 | 87.81 | 83.68 | 86.97 | 93.51 | 86.06 | 86.63 | 84.78 | 84.32 | 92.19 | 85.81 | 89.05 | 87.21 | 90.44 | 90.35 | 91.23 | 91.01 | 96.95 |
| YN01429 | 87.31 | 83.52 | 85.85 | 92.92 | 85.30 | 87.68 | 83.09 | 84.13 | 92.95 | 86.86 | 90.62 | 87.45 | 91.19 | 91.34 | 91.37 | 93.29 | 97.13 |
| Yellow Checks | 87.56 | 83.60 | 86.41 | 93.21 | 85.68 | 87.16 | 83.94 | 84.22 | 92.57 | 86.34 | 89.84 | 87.33 | 90.81 | 90.85 | 91.30 | 92.15 | 97.04 |
| 46A65 | 86.09 | 82.27 | 84.28 | 91.19 | 85.23 | 84.87 | 81.49 | 81.96 | 89.67 | 83.44 | 86.78 | 87.00 | 88.34 | 88.72 | 88.89 | 91.17 | 96.14 |
| Q2 | 87.19 | 84.99 | 87.50 | 93.42 | 87.62 | 87.16 | 85.05 | 85.87 | 92.87 | 87.35 | 90.56 | 88.39 | 90.98 | 90.22 | 91.30 | 91.80 | 97.09 |
| Black Checks | 86.64 | 83.63 | 85.89 | 92.31 | 86.42 | 86.02 | 83.27 | 83.91 | 91.27 | 85.40 | 88.67 | 87.69 | 89.66 | 89.47 | 90.09 | 91.49 | 96.61 |
| Nex 822 CL | 92.50 | 89.39 | 91.12 | 95.90 | 90.09 | 92.94 | 89.64 | 90.60 | 95.87 | 92.52 | 94.68 | 91.25 | 94.63 | 93.57 | 94.12 | 93.38 | 97.31 |

TABLE 22

Mean True Metabolizable Energy of canola meal corrected to 0% oil content

| Line | Mean TMEn Oil Free |
|---|---|
| YN97262 | 2650 |
| DN041593 | 2638 |
| Nex 822 CL | 2580 |
| DN041279 | 2573 |
| DN041506 | 2482 |
| DN041510 | 2471 |
| DN041495 | 2459 |
| DN041537 | 2425 |
| YN01429 | 2424 |
| DN041667 | 2414 |
| 46A65 | 2248 |
| Q2 | 2230 |

REFERENCES

Bell, J. M., Shires, A. 1982. Composition and digestibility by pigs of hulls fractions from rapeseed cultivars with yellow or brown seed coats. Can. J. Animal Science 62:557-565.

American Oil Chemists' Society (AOCS) Official Methods Am 2-92 Oil content in Oilseeds AOCS Official Methods Ba 4e-93 Combustion Method for the Determination of Crude Protein AOCS Official Method Ak 1-92 (93) Determination of glucosinolates content in rapeseed and canola by HPLC Bell, J. M. 1993. Feeding studies of yellow-seeded Brassica. Can. J. Animal Sci. 73:679-697.

Bell, J. M. 1995. Meal and by-product utilization in animal nutrition, pp. 301-337. In: Brassica oilseeds, production and utilization. Ed. D. Kimber and D. I. McGregor. Cab International, Wallingford, Oxon, OX108DE, UK.

Getinet, A., G. Rakow. 1997. Repression of seed coat pigmentation in Ethiopian mustard. Can. J. Plant Sci. 77:501-505.

Newkirk, R. W., H. L. Classen and M. J. Edney. 2003. The digestibility and content of amino acids in toasted and non-toasted canola meals. Canadian Journal of Animal Sci. 83:131-139

Rakow, G., Relf-Eckstein, J., Raney, P. and Gugel, R. 1999a. Development of high yielding, disease resistant, yellow-seeded Brassica napus. Proc. 10$^{th}$ Int. Rapeseed Congress, Canberra, Australia, Sep. 26-29, 1999. Oral presentation, session C 07.

Rakow, G., Raney, P. and Relf-Eckstein, J. 1999b. Agronomic performance and seed quality of a new source of yellow-seeded Brassica napus. Proc. 10$^{th}$ Int. Rapeseed Congress, Canberra, Australia, Sep. 26-29, 1999. Poster #9.

Rakow, G., J. P. Raney. 2003. Present status and future perspectives of breeding for seed quality in Brassica oilseed crops. Proc. 11$^{th}$ Int. Rapeseed Cong., Copenhagen, Denmark, 6-10 Jul. 2003, 1:181-185, oral keynote (invited).

Rakow, G. (2004a). Canola meal quality improvement through the breeding of yellow-seeded varieties—an historical perspective. AAFC Sustainable Production Systems Bulletin. 2 pp.

Rakow, G. (2004b). Yellow-seeded Brassica napus canola for the Canadian canola Industry. AAFC Sustainable Production Systems Bulletin. 2 pp.

Rashid, A. and Rakow, G. 1995. Seed quality improvements in yellow seeded Brassica napus. Proc. 9$^{th}$ hit. Rapeseed Congress, Cambridge, England, Jul. 4-7, 1995. Vol. 4: 1144-1146.

Rashid, A., Rakow, G. and Downey, R. K. 1994. Development of yellow-seeded Brassica napus L. through interspecific crosses. Plant Breeding 112: 127-134.

Relf-Eckstein, J., G. Rakow and J. P. Raney 2003. Yellow-seeded Brassica napus canola—anew generation of high quality canola for Canada. Proc. 11$^{th}$ Int. Rapeseed Congress, Copenhagen, Denmark, Jul. 6-10, 2003. Vol. 2: 458-460.

Shirzadegan, M., G. Röbelen. 1985. Influence of seed color and hull proportion on quality properties of seeds in Brassica napus L. Götingen Fette Seifen Anstrichmittel 87:235-237.

Simbaya, J., Slominski, B. A., Rakow, G., Campbell, L. D., Downey, R. K. and Bell, J. M. 1995. Quality characteristics of yellow-seeded Brassica seed meals: protein, carbohydrate and dietary fiber compounds. J. Agr. Food Chem. 43: 2062-2066.

Slominski, B. A., Campbell L. D. and Guenter, W. 1994. Carbohydrates and dietary fiber components of yellow-seeded and brown-seeded canola. J. Agric Food Chem. 42:704-707

Stringham, G. D., McGregor, D. L. and Pawlowski, S. H. 1974. Chemical and morphological characteristics associated with seed coat color in rapeseed. In Proceedings of the 4$^{th}$ International Rapeseed Congress, Giessen, Germany pp. 99-108.

The invention claimed is:

1. A canola plant that produces yellow-coated seeds having at least 68% oleic acid (C18:1) by weight and less than 3% linolenic acid (C18:3) by weight, relative to total C12, C14, C16, C18, C20, C22, and C24 fatty acids, wherein said plant is grown from seed available under an ATCC deposit number selected from PTA-6806 and PTA-6807.

2. The plant of claim 1 wherein said seeds have acid detergent fiber below 11% as determined by NIR on a dry mass basis.

3. The plant of claim 1 wherein said seeds comprise at least 43% oil by weight.

4. The plant of claim 1 wherein said seeds comprise at least 45% protein by weight.

5. The plant of claim 1 wherein said seeds comprise at least 43% oil by weight and at least 45% protein by weight on a dry mass basis determined using NIR.

6. A population of plants according to claim 1 wherein said plants yield at least 1700 kilograms of seed per hectare.

7. A progeny plant of claim 1 wherein said progeny plant produces yellow-coated seeds having at least 68% oleic acid (C18:1) and less than 3% linolenic acid (C18:3) by weight, relative to total C12, C14, C16, C18, C20, C22, and C24 fatty acids.

8. A seed produced by the canola plant of claim 1.

9. A plant grown from the seed of claim 8.

10. Animal feed comprising meal of seeds according to claim 8.

11. The plant of claim 1 wherein said plant was produced without genetic engineering and without mutagenesis.

12. Canola meal produced from seeds according to claim 1.

13. The meal of claim 12 wherein said meal has a mean true metabolizable energy of at least 2400 kcal/kg.

14. The plant of claim 1 wherein said seeds have reduced antinutritional components compared to Nex 705 seeds or yellow seeds lines YN97-262 and YN9562.

15. The plant of claim 14 wherein said seeds have a phytate content of less than 1.3%, an acid detergent lignin content of less than 2%, and a neutral detergent fiber content of less than 17%.

16. The plant of claim 1 wherein said seeds comprise a meal component having at least 47% protein by weight.

17. The plant of claim 1 wherein said seeds comprise at least 43% oil by weight and a meal component having at least 47% protein by weight on a dry mass basis determined using NIR.

18. The meal of claim 12 wherein said meal has at least 47% protein by weight.

19. An F1 generation plant produced from the plant of claim 1, wherein said F1 generation plant produces yellow-coated seeds having at least 68% oleic acid (C18:1) by weight and less than 3% linolenic acid (C18:3) by weight, relative to total C12, C14, C16, C18, C20, C22, and C24 fatty acids.

* * * * *